(12) United States Patent
Nagura et al.

(10) Patent No.: US 7,499,809 B2
(45) Date of Patent: Mar. 3, 2009

(54) PARTICLE SIZE DISTRIBUTION ANALYZER

(75) Inventors: Makoto Nagura, Kyoto (JP); Yuki Ishii, Kyoto (JP); Hideyuki Ikeda, Kyoto (JP); Takuji Kurozumi, Kyoto (JP); Yoshiaki Togawa, Kyoto (JP)

(73) Assignee: Horiba, Ltd., Kyoto (JP)

(*) Notice: Subject to any disclaimer, the term of this patent is extended or adjusted under 35 U.S.C. 154(b) by 431 days.

(21) Appl. No.: 11/214,581

(22) Filed: Aug. 30, 2005

(65) Prior Publication Data
US 2006/0052944 A1 Mar. 9, 2006

(30) Foreign Application Priority Data

Aug. 30, 2004 (JP) ............................ P2004-251095
Aug. 31, 2004 (JP) ............................ P2004-252230
Aug. 31, 2004 (JP) ............................ P2004-253650

(51) Int. Cl.
*G01N 31/00* (2006.01)
(52) U.S. Cl. ...................................... 702/29
(58) Field of Classification Search .................. 702/29; 73/865.5; 356/335, 336
See application file for complete search history.

(56) References Cited

U.S. PATENT DOCUMENTS 4,665,760 A * 5/1987 Eramo et al. ............... 73/866.5
4,890,920 A * 1/1990 Niziolek et al. ............. 356/336

FOREIGN PATENT DOCUMENTS

| JP | 6-82546 | 11/1994 |
|---|---|---|
| JP | 07-294411 | 11/1995 |
| JP | 2000-146814 | 5/2000 |
| JP | 2000-214068 | 8/2000 |

* cited by examiner

*Primary Examiner*—Bryan Bui
*Assistant Examiner*—Stephen J Cherry

(57) ABSTRACT

In a measurement system, by suppressing the environmental changes of counter-flow of air, and temperature changes and the like, measurement can be accomplished with stable high precision and replication, and by providing a transparent cell 2 which stores a particles dispersed in a dispersion medium, and a light source which irradiates light onto the particles within the transparent cell 2, and multiple light detectors 5 scattered and arranged to detect the intensity of diffracted/scattered light produced by the irradiation of light, and a computer device 6 which calculates the particle size distribution of the particles based on the light intensity signal output from the light detectors 5, in addition to the establishment of cell storage space S which stores the transparent cell 2 and the equipment storage spaces S1 and S2 which store the light source 41a, the light detector 5, and the optical device 6, the equipment storage spaces S1 and S2 are given tight closed construction separate from the cell storage space S.

27 Claims, 18 Drawing Sheets

PARTICLE SIZE DISTRIBUTION ANALYZER

BACKGROUND OF THE INVENTION

1. Field of the Invention

The present invention relates to a particle size distribution analyzer in which measurement of the particle size distribution is accomplished based on the strength of the diffracted and/or scattered light (hereafter referred to as diffracted/scattered light) by irradiating light onto the particles distributed within the dispersion medium.

2. Background of the Related Art (1) This type of particle size distribution analyzer such as is disclosed in Japanese Laid Open Patent 2000-146814 irradiates light from the light source of a laser and the like onto a particle stored in transparent cells, and the intensity angle distribution of the diffracted/scattered light generated at the time is detected by multiple light detectors dispersed and arranged on the periphery of the cells, in order to measure the particle size distribution of the particles based on the detected results.

Heretofore, in addition to housing a light source, or light detector, or optical system equipment between the two in a single case, a cell storage space (so-called sample chamber) has been arranged in the center of the case, so as to arrange the cells.

However, as shown in the publication, making the light source side to be of sealed construction is already known, and since the cell storage space is frequently opened by the user to accomplish cell exchange and the like, completely sealed construction is not achieved, and in reality is coupled with the space in which the detector is arranged. As a result, the space on the detector side is spatially connected to the cell storage space (sample chamber), with vacillation of the light on the light detector side being caused by counter currents of air or changes in temperature, making it difficult to make measurements with good replication.

(2) In addition, as shown in the same publication with regard to various particle size distribution analyzers, from a construction standpoint, as shown in the scaled plane diagram of FIG. 13, the light source or the light detector, or the optical system equipment located between them, is housed in a single case, in addition to which a cell storage space (a so-called sample chamber) is provided in the center of the case so as to arrange the cells. In the cell, there are various types of dispersion media, such as liquid bodies of water or alcohol, with the presence of various gaseous bodies of air and the like, classified as being wet and dry, and the dispersion medium and granules are also classified as being either a flow type or batch type, depending upon whether or not they are circulated.

With the construction referred to above, since the sample chamber is surrounded on the periphery by other equipment, access to the sample chamber is only available from above, and given the limit to the space above, since the breadth of the space is inadequate, operations such as changing the cell type in switching the measurement format, or washing the cells as part of maintenance and the like, makes for extremely poor operability when there is a need to also remove not only the cells, but also the cell holder which supports the cells. As a result, depending upon the circumstance, there are also cases in which the sample chamber itself must be removed and exchanged.

Furthermore, heretofore, in addition to basically housing the measurement system devices of a light source and light detector and the like in a single case, since there is the concept of attaching a sample chamber within the case, devising construction with airtight separation between the sample chamber within the case and other space is extremely difficult. Given the premise of such construction, even adopting a new measurement format in which spraying is performed within the sample chamber and the sprayed granule diameter is measured, there is the problem of the spray reaching the detector, making it difficult to easily adopt the new format.

In other words, in conventional devices, there was the difficulty that the construction itself became a bottleneck, with poor operability, making it difficult to introduce newly developed measurement formats.

(3) On the other hand, in Japanese Laid Open Patent Publication 2000-214068, reference is made to an example of this type of particle size distribution analyzer in which light emitted from the light source of an He—Ne laser and the like is introduced to a beam expander through a mirror, and the diameter is widened and following irradiation of the light onto the particles in the cell, generated diffracted/scattered light is received through a lens by the scattered and arranged light detectors.

With such a device, when accomplishing measurement of particle size distribution with good precision up to and including large diameter particles, detection must be accomplished also of diffracted/scattered light which has an extremely small angle from the light axis. Owing to this, the detector must be arranged extremely close to the vicinity of the optical axis, greatly increasing angle resolution ability. With such construction, it is necessary that there be accurate positional alignment of the light from the light source, and the detector.

Heretofore, in accomplishing the referenced positional alignment in the production process, the mirror is adjusted on an optical bench, and optical axis alignment is performed between the light source and the beam expander. Subsequently, in order to individually accomplish positional alignment of the lens and light detector, simultaneous fixing and adjustment must be accomplished on the optical bench for each product, which is laborious.

Furthermore, in accomplishing positional alignment, since the use of the interfering light between the light emitted from the light source and other optical products not only requires manual operation and time, there is also great concern that required skillfulness will result in aberrations produced by the operator.

In addition, when accomplishing maintenance to exchange the light source and the like as well, due to duly consider minute differences between the pre-exchange light source and the post exchange light source, in addition to the exchange, there is a need to re-adjust the entire body of the optical system, with the added inconvenience of requiring a great amount of time and effort.

SUMMARY OF THE INVENTION (1) With the present invention, in this type of particle size distribution analyzer, a primary object is the performing of measurements, the good replication of which have a high level of stability, through entirely new construction, in which changes such as the counter flow of air or temperature changes in the measurement system can be suppressed.

The particle size distribution analyzer relating to the present invention in order to resolve such problems is characterized by being provided with a transparent cell which stores a particles dispersed in a dispersion medium; and a light source which irradiates light onto the particles within the transparent cell; and multiple light detectors dispersed and arranged so as to detect the intensity of diffracted/scattered light generated by the emission of light; and optical equipment arranged between the light source and the light detectors, and calculates the particle size distribution of the particles based on light intensity signals output from the optical detector, and in addition to attaching mechanical storage space which provides cell storage for storing the transparent cell, the light source, the light detectors, and the optical equipment, has sealed construction in which the cell storage space and the mechanical storage space are mutually separated.

Moreover, since the equipment storage space which stores the light source, light detector, and optical equipment has sealed construction, there can be airtight separation in relation to the cell storage space which the user can open and close, and temperature changes, counter flow of air, and abnormal mixing and the like is prevented, stabilizing the internal environment, and making it possible to conduct measurements with high stability and good replication. In addition, maintenance can be realized over an extended period of time.

On the other hand even if such equipment storage space is tightly sealed, if equipment such as a motor or fan or an actuator or the like is also stored, then the heat generated from them becomes a source of environmental instability. In order to avoid this, it is desirable to arrange equipment such as motors or fans or the like outside of the equipment storage space. In addition, concerning the need to arrange and move movable mirrors or shutters and the like to within the equipment storage space, the actuator is set outside of the equipment storage space, and it would be well if the actuator is driven by a drive transmission mechanism which passes through the outer wall forming the equipment storage space.

If the equipment storage space is tightly sealed, in stabilizing the internal environment, it becomes undesirably difficult to seal if the capacity becomes too large. Owing to this, it would be well to partition the equipment storage space, through the attachment of multiple cases. However, if the cases are separately arranged, if there is slippage in the position assembly between the cases, then the positional relationship between the apportioned storage of the light source and light detector also slips, with the concern that a great deal of care will be required in terms of assembly and maintenance.

In order to resolve this, it is desirable that the analyzer further comprises a base construction body which accomplishes unitized construction and a couple of cases which are mutually separately arranged, using the base construction body, wherein the equipment storage is formed by the cases in which the light source, the light detectors and the optical equipment are separately arranged, the cell storage space is arranged between the cases.

In order to providing for the coexistence of operability and sealing the cell storage space, it is desirable that in surfaces forming the cell storage space, at least two surfaces next to each other are provided with attached open shut lids which can be respectively opened and closed, and that the construction is such that, in a state in which the open shut lids are open, the two surfaces form a continuous aperture.

More specifically, the two aperture surfaces comprising the upper surface of the cell storage space and the front surface are desirable from the standpoint of operability.

As a specific example of an execution for arranging power equipment to be on the outside, the optical equipment is provided with a projection lens which refracts the light which broadens from the light source, further comprises a mechanical open shut tight shutter being arranged between the light source and the projection lens, and a drive source of the shutter being arranged on the outside of the equipment storage space.

(2) In addition, with this type of a particle size distribution analyzer, this invention provides entirely new construction, by which, in addition to greatly improving the operability within the cell storage space (sample chamber), it enables the flexible introduction of a new measurement format, corresponding to handling the 2nd issue of future development.

The particle size distribution analyzer relating to the present invention is comprising, a transparent cell which stores a particles dispersed in a dispersion medium; a light source which emits light onto the particles within the transparent cell; multiple light detectors dispersed and arranged so as to detect the intensity of diffracted and/or scattered light (hereafter referred to as diffracted/scattered light) generated by the emission of light from the light source; a computer device which calculates the particle size distribution of the particles based on light intensity signals output from the light detectors; a couple of cases being arranged to be mutually separated, which provide apportioned storage of the light source and light detectors, and a cell storage space which passes to an opposing surface from one surface, being formed between the facing walls of both cases.

With such construction, each case can be arranged, for example, with lateral separation and by establishing a front to rear pass-through direction, making it possible for there to be operability not only from above the also from the front to rear, greatly improving the operability within the cell storage space.

In addition, since forming the cell storage space outside of the cases is an entirely new concept, airtight separation can be easily maintained between the cell storage space and the cases, and, for example, new measurement formats can be easily introduced for measuring the sprayed granule diameter, by, spraying between the cell storage space. Furthermore, since the two cases are separated, in the design stages for changing the positional arrangements, various variations can be considered which are extremely beneficial to future development.

On the other hand, if in this manner construction is provided in which the cases interspersed between the cell storage area are separately arranged, if there is slippage in the assembled position between the cases, slippage also will occur in the positional relationship between the apportioned storage of the light source and light detector, and depending upon circumstance, the final optical adjustment stage will be unable to absorb the positional slippage, requiring corrective reassembly.

In order to avoid such an inconvenience, a base construction body is provided, formed from a standing support body which stands as a unit at both ends of the interim body, and in addition to providing apportioned support of the light source and light detector by each standing support body, it is desirable that the case be formed using at least a part of each standing support body.

In addition to maintaining the temperature to be fixed to the extent possible, and achieving improved measurement precision and stability by preventing the convection flow of internal air, in addition to accomplishing the sealed closed construction of each case, it is desirable that heat separation be accomplished by arranging heat generating actuators and electrical sources outside of the case, and that within the case use be made of only such construction members as light sources, light detectors, or optical system equipment.

In establishing coexistence between operability and sealing between the cell storage spaces, it is desirable that among surfaces forming the cell storage space, are attached open shut lids capable of being open and shut on at least 2 surfaces which include either said one surface or its opposing surface, in addition to which the other surfaces are blocked, with construction being accomplished so as to be able to seal the cell storage space. In particular it is more desirable that the open surfaces are closely proximate, and in the open state the surfaces of the open shut lids are contiguous.

Specifically, it would be desirable from the standpoint of operability if the 2 open surfaces be the upper surface and the front surface of the cell storage space.

Activating the characteristics of the cell storage space relating to the pass through characteristic of the present invention in order to foster the effect of improved operability of the present invention, a cell support mechanism is provided in which multiple cells are movably maintained in a pass-through direction, and if construction is provided in which light from a light source radiating on at least one cell can be selectively positioned in the light radiating position, by simply switching to another measurement format cell exchange can be accomplished by only sliding, and without removing and exchanging the cell.

(3) Furthermore, the present invention has a third primary object of making it so that positional alignment of the measurement system devices from a light source to the light detector could be easily and accurately accomplished by anyone within a short period.

Corresponding to the subject problem, the particle size distribution analyzer relating to the present invention is characterized by being comprising a light source which irradiates light to the particles; a light detector which detects the intensity of diffracted/scattered light generated by the radiation of light; a calculating part which calculates the particle size distribution of the particles based on the output value from a light detector; a base construction body comprising a single product; a support body which forms a light source unit which supports as a unit the light source and projection lens arranged in front of the light source; a light track adjustment mechanism for adjusting the tracking of the light emitted from the light source attached to the light source unit; and position determination construction for positioning and attaching the light source unit and the light detectors in a specified position of the base construction body.

With such a mechanism, in addition to unitizing the light source and projection lens, since an optical track adjustment mechanism is attached to the light source, separate light track adjustment can be accomplished with the light source unit body. If the optical axis adjustment has, for example, an attached specialized jig (hereafter referred to as a light track confirmation tool), it can be easily used by anyone. In addition, if light track adjustment is accomplished in this manner, subsequent use can be made of position determination construction, by which anyone could easily and accurately attach a light source unit and light detector relative to the base construction body in a short time. Therefore, there is substantial improvement in the operability and quality of the device in comparison with the time required to manufacture a device under the prior art.

Furthermore, interchangeability is maintained even while adjusting the optical track for each light source unit. In other words, in order to achieve uniform quality, and to accomplish, for example, interchangeability of the light source units, it is no longer necessary to accomplish individual light adjustment, and great operability is also obtained in terms of maintenance time.

In addition, the particle size distribution analyzer relating to the present invention is characterized by being provided with a light source which irradiates light to the particles; a light detector which detects the intensity of diffracted/scattered light generated by the radiation of light; a calculating part which calculates the particle size distribution of the particles based on the output value from a light detector; a base construction body comprising a single product; a support body which forms a light source unit which supports as a unit the light source and projection lens arranged in front of the light source; a light track adjustment mechanism for adjusting the tracking of the light emitted from the light source attached to the light source unit; a second support body which supports the light detectors, and forms the detector unit; and a detector position adjustment mechanism for adjusting the light detectors unit to a predetermined position of the second support body; and position determination construction for positioning and attaching the light source unit and the light detector unit in a specified position of the base construction body.

With such construction, the light detector is also unitized with position adjustment capability, and since it can be said to further assume unitization in optical measurement devices, the mentioned effects are significant.

On the other hand, as an appropriate manufacturing method for a particle size distribution analyzer having such construction, comprises the steps of adjusting the light track relative to the light source unit by the light track adjustment mechanism so as to be brought to within standards, by using a light tracking confirmation jig which is capable of recognizing whether the light track from the light source unit is within standards; and attaching the post-adjustment light source unit to the base construction body.

Furthermore, in case that the method comprises the steps of adjusting the relative position of the light detectors to the second support body by the detector position adjustment mechanism so as to be brought to within standards, by using a detector position confirmation jig which is capable of recognizing whether the relative position of the light detectors are within standards; and attaching the post-adjustment light detector unit to the base construction body, the effect of the present invention becomes remarkable.

DETAILED DESCRIPTION OF THE PREFERRED EMBODIMENTS

Each Embodiment of the present invention is described hereafter, with reference to the Drawings.

(1) First Embodiment

Overall Summary

Figure 1:
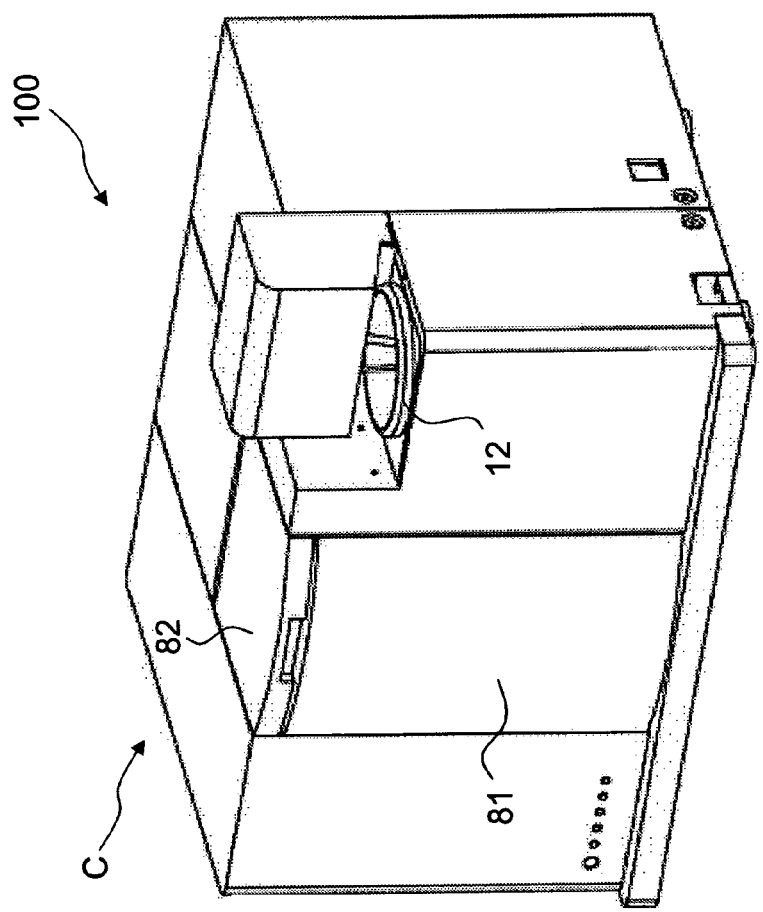
FIG. 1 is an overall oblique diagram showing the main body of the particle size distribution analyzer of Embodiment 1 of the present invention.
Figure 2:
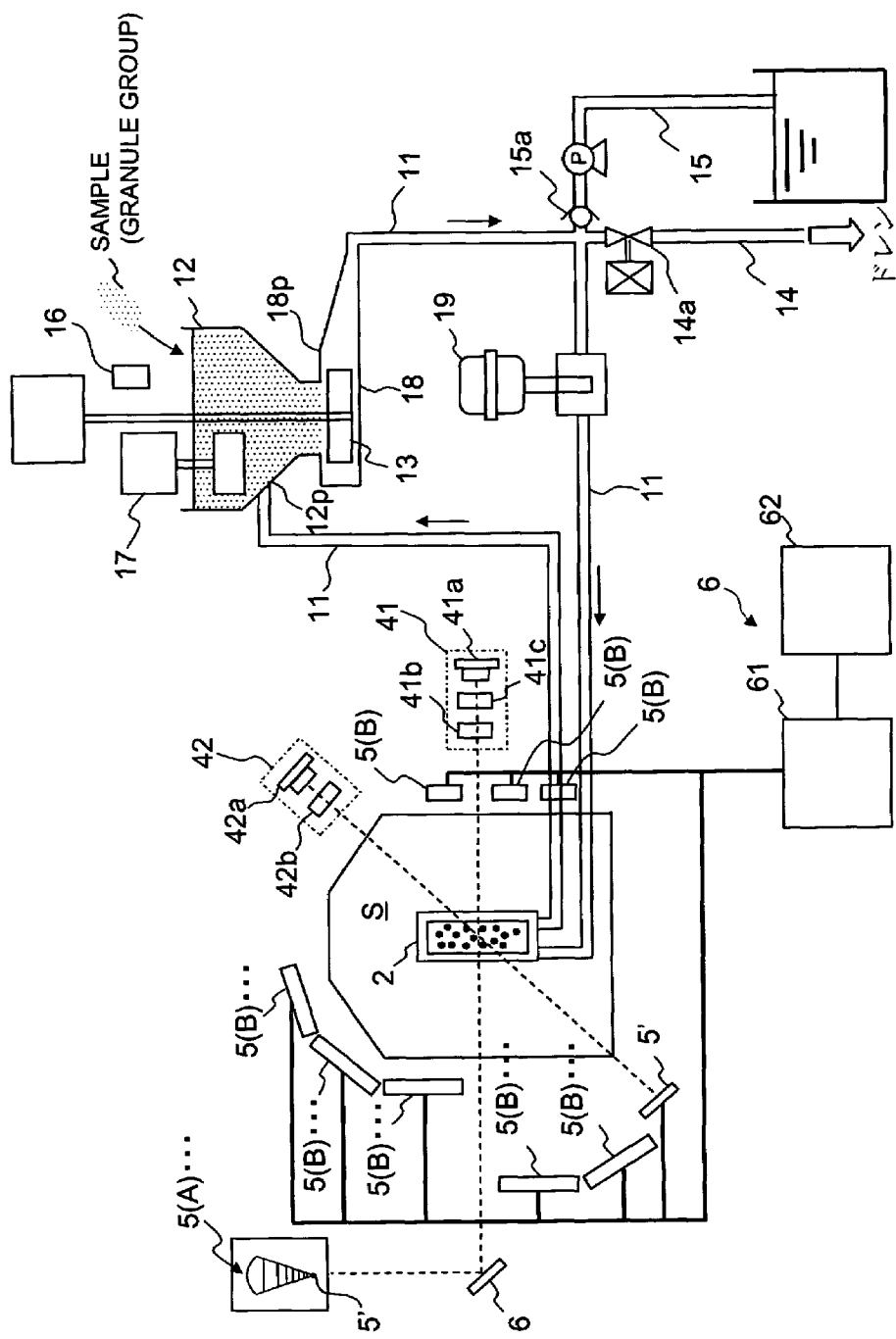
FIG. 2 is a scaled mechanical construction diagram showing the particle size distribution analyzer of the same Embodiment.

In the particle size distribution analyzer 100 relating to the first Embodiment of the present invention, as shown in FIG. 1, which shows an external view of the device, and in FIG. 2 which shows a scaled diagram of the internal function construction, detection is accomplished of the diffracted scattered pattern (angular distribution of the diffracted/scattered light intensity) generated at the time light is irradiated onto the particles which is the subject of measurement, reverse Fourier exchange calculations are executed based on the MIE from the diffracted scattering pattern, and measurements are made of the particle size distribution. If it is understood to be large, then it is provided with various measurement system devices, circulation system devices, computer system devices, construction devices and miscellaneous other supplementary devices.

Various Measurement System Devices

Various measurement system devices, as shown in FIG. 2, include transparent cells 2 which store the particles dispersed in a dispersion medium, a light source which irradiates light onto the particles within the transparent cells 2, and multiple light detectors 5 separately arranged to detect the intensity of diffracted/scattered light produced by the radiation of light.

Cell 2 is, for example, made of resin, and specifically, as described hereafter supports different types of multiple cells (for example, wet flow cells, dry type batch cells, and dry type cells; in FIG. 2, only the wet type flow cells are shown) in a movable manner by means of the cell support mechanism 3 (not shown in FIG. 2) described hereafter, and is constructed so as to switch the cell 2 to be measured.

To the light source is attached, for example multiple (two types of) switchables. The first light source is a semiconductor laser 41, which produces red laser light of a wavelength of, for example, approximately 650 nm. The second light source is an LED 42a, which produces blue light of a wavelength of, for example approximately 400 nm. When measuring a granule having a large granular diameter, it is beneficial for there to be light having a long wavelength. Since, when measuring granules having a small granule diameter, it is beneficial for the light to have a short wavelength, by attaching multiple light sources 41a and 42a which produce lights of differing wavelengths, the measurable range of the granule diameter becomes broader without any loss of precision. In this instance, in addition to setting the optical axis of the laser light to be horizontal, the optical axis of the LED light can be said to be inclined, and by making the light axes to intersect in roughly the center of cell 2, the intersecting position becomes the light radiation position relative to the particles within cell 2.

On the light projection side of each light source 41a, 42a are respectively arranged light projection lenses 41b, 42b. Also, light emitted while becoming broader from the light sources 41a, and 42a is refracted and converged by the projection light lenses 41b and 42b, so as to irradiate the cells 2. In this embodiment, light sources 41a and 42a and projection light lens 41b and 42b are structured as a single unit, becoming the light source units 41 and 42.

Figure 3:
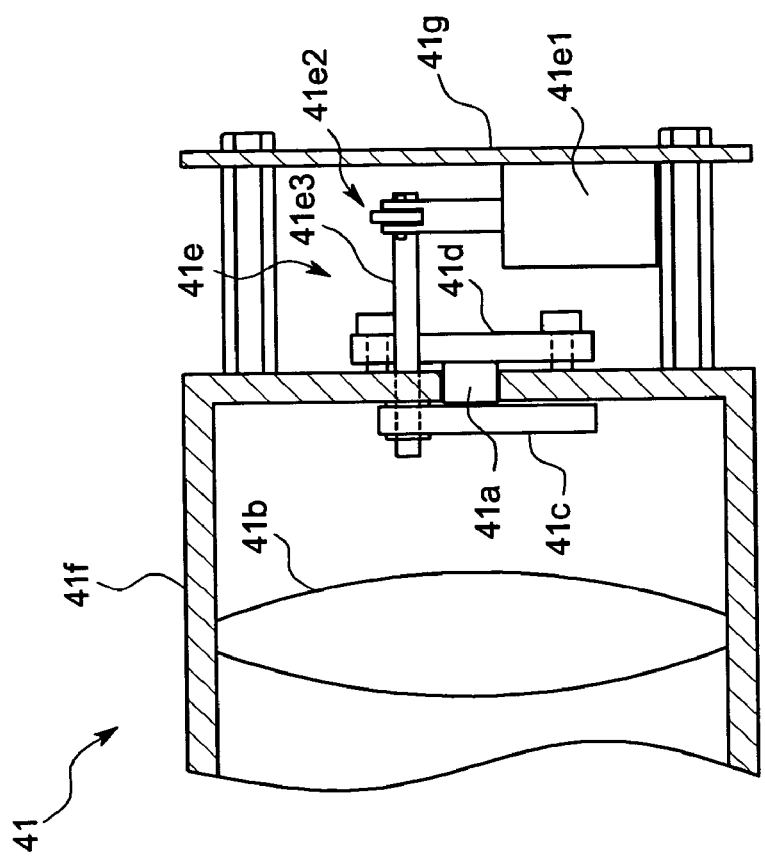
FIG. 3 is a vertical scaled cross-sectional diagram showing the open shut shutter construction of the same Embodiment.
Figure 4:
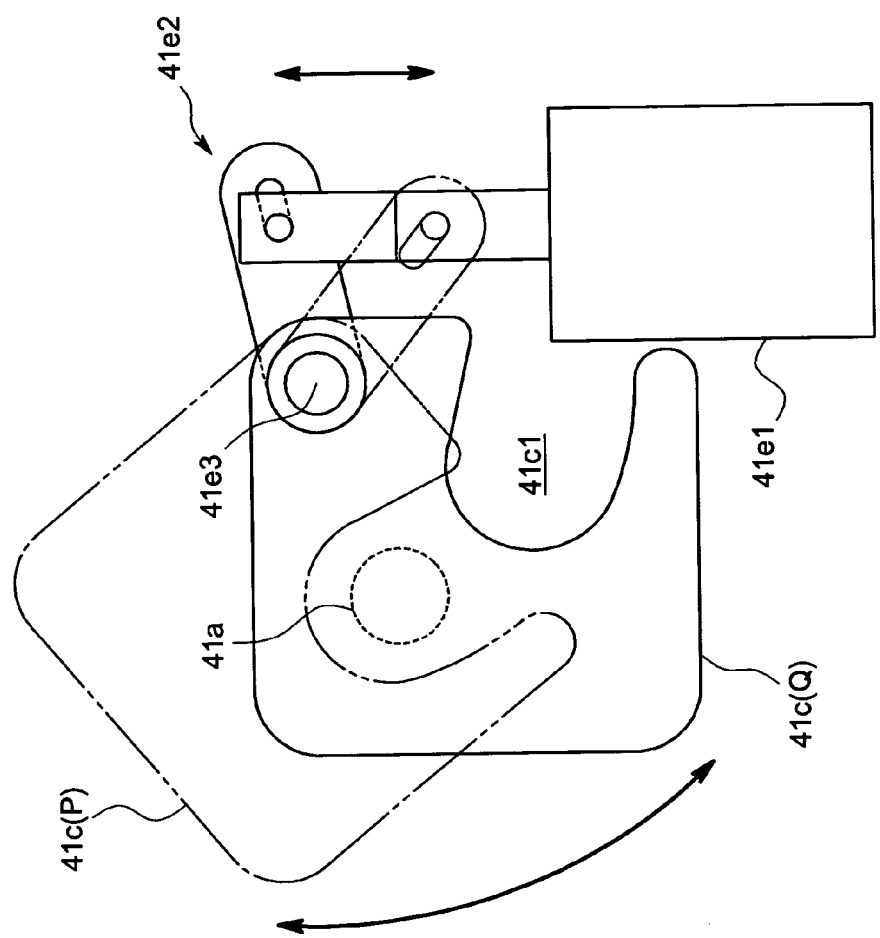
FIG. 4 is a scaled construction diagram showing the open shut operation of a shutter in the same Embodiment.

The laser light source unit 41, as shown in a scaled format in FIG. 3 and FIG. 4, is composed of a semiconductor laser 41a and a substrate 41d which mounts the semiconductor laser 41a, a projection lenses 41b, a cylindrical storage body 41f which stores the projection lenses 41b, a shutter 41c attached between the semiconductor laser 41a and the projection lens 41b within the storage body 41f, and a drive mechanism 41e which drives to open and shut the shutter 41c, and unitizes the attachment member 41g which is attached as a unit to storage body 41g. The drive mechanism 41e is formed from the direct drive type electromagnetic actuator 41e1 and the transmission conversion mechanism 41e2 which transmits the movements of the direct drive type electromagnetic actuator 41e1 to the open shut operation of the shutter 41c, and the electromagnetic actuator 41e is attached so as to be positioned outside of the storage body 41f. The shutter 41c forms a rectangular plate with an attached diagonal cut out 41c1, as shown in the example of FIG. 4, and the bottom wall of the storage body 41g passes through and is fixed at the corner of the rotatable support axis 41e3 (a part of the transmission conversion mechanism 41e2). Also, the support axis 41e3 operated by the electromagnetic actuator 41e1 connected to the support axis 41e3, by means of positive and reverse rotation rotatably operates between the opening forming position P, with the shutter 41c being provided with a cut out 41c1 positioned in the front surface of the semiconductor laser 41a, and the light shielding position Q which shades the laser light, positioning the rectangular plate to the front surface of the semiconductor laser 41a, so that the laser light can transmit. The lower part 41e2 than the cut out 41c1 in the rectangular plate acts as a vertical, and even in the case when the electromagnetic actuator is not operating, it functions as a fail safe mechanism so that by means of the vertical it is always brought to the light shielding position Q.

LED light source unit 42, as shown in the scaled format of FIG. 2, is unitized, and stores an LED 42a, a substrate (not shown) which mounts the LED 42a, and projection lenses 41b and 42b, in a second storage body (not shown).

Also, when measuring the particle size distribution, using LED 42a, in addition to point lighting the LED 42a, the shutter is closed, shielding light from the semiconductor laser 41a. When measuring the particle size distribution using the semiconductor laser 41a, in addition to opening the shutter 41c, the LED 42a is extinguished. Allowing the light to remain lit, without extinguishing the semi conductor laser 41a is done to prevent the output of the semi conductor laser 41a from being changed by the point reduction.

The light detector 5 uses a photodiode and the like, and outputs an electrical signal (light intensity signal) of a strength corresponding to the intensity of the received light.

The total number of light detectors 5 is between 9-100, which are scattered and arranged on a vertical surface in the periphery of the cell 2 and includes the cell 2. Particularly, in this state, the light detectors 5 are classified into narrow angle scattered light detectors 5(A) for detecting with good precision the angle of diffracted/scattered light at a small angle less than a fixed angle, and a wide angle scattered light detector 5(B) for detecting diffracted/scattered light rearward and from the side from the front at wider than a fixed angle. Narrow angle scattered light detectors 5(A) are tightly arranged in the same circular shape with an extremely narrow width on a substrate, in a ring detector array, with the wide angle scattered light detectors 5(B) being blocked in multiple units, or independently scattered and arranged. Moreover, the length of the light path having abbreviated space extends to the narrow angle scattered light detector group 5(A), and is arranged so that the diffracted/scattered light is led through a movable mirror 6, in order to enable minute adjustments.

In addition, to the optical axis of each light source 41a and 42a is respectively attached a transmitted light detector 5' for detecting the intensity of the transmitted light, and light which passes the projection optical lenses 41b and 42b converges on the light receiving surface of the transmitted light detector 5'.

Circulation System Devices

Circulation system device types are device types for accomplishing the circulation supply of liquid samples in which particles are dispersed in dispersion media (water or alcohol) in a wet type flow cell 2. In this embodiment, as shown in FIG. 2, at a minimum there is an attached circulation pipe 11 which forms a circulation path for circulating the liquid sample, and a circulation bath 12 attached on the circulation path used for injecting the sample, and a circulation pump 13 for circulating the sample within the circulation path.

The circulation pipes 11 forms a closed circulation path, and attaches a wet type flow cell 2 or circulation bath 12 to the circulation system path. To the circulation pipe 11 is connected a non-aqueous use pipe 14 or dispersion media supply pipe 15 connected through valves 14a and 15a. In this instance, the dispersion media supply valve 15a, as with the non-aqueous valve 14a is attached in the lowest position on the circulation path, and the dispersion medium is supplied to the circulation path while extracting air from below. The combining of air into the dispersion media and at the time of supply is prevented to the extent possible.

The circulation bath 12 forms an abbreviated route as the upper surface sample injection opening, and is attached to the uppermost part of the circulation path. To the circulation bath 12 is attached a water level sensor 16 of the multi-point detection type-continuous detection type. While detecting the water level by means of the water level sensor 16, the supply valve 15a and the non-aqueous valve 14a is controlled, construction being such that the concentration of the liquid sample is automatically adjusted. In addition, to the circulation bath 12 is attached a motor used for agitation.

The circulation pump 13 is a centrifugal type, internally housed in a pump chamber 18, which extends and is connected to the lower end of the circulation bath 12. Also, the low flow end of the circulation pipe 11 is connected to the intake port 12 attached to the side surface of the circulation bath 12, and the upper flow end of the circulation pipe 11 is connected to the exhaust port 18 attached to the side surface of the pump chamber 18. If the circulation pump 13 is operating, the liquid sample is pressure sent from the exhaust port 18, and circulates on the circulation path, the intake port 12 being constructed so as to pass through the circulation bath 12, and return to the pump chamber 18. Moreover, the label 19 attached to the circulation system path is an ultra-sonic wave oscillator used, for example, to separate any occurring cohesion of the particles.

Computer Equipment System Types

As computer system equipment types, as shown in FIG. 2, there is an attached main body computer 61 to which is communication capably connected an information controller 62.

The main body computer 61 is a specialized computer circuit housed within a main casing C, described hereafter. Primarily, the optical intensity signal from each light detector 5 is pre-amplified, and incorporated through an A/D converter, and the granule distribution is computed, or is run until it is computed, and the resultant data is sent to the information controller 62. Other than that, control of each of the previously mentioned devices is accomplished or other data is acquired and computations performed based on commands from the information controller 62.

The information controller 62, is for example, an all-purpose computer, which accomplishes communication with the main body computer 61, and through the operation of the operator, or automatically, displays the particle size distribution measurement results in various states, or calculation parameters are established, and control is accomplished of each of the various devices through the main body computer 61.

Moreover, the main body computer 61 and the information controller 62 form a computer 6, which operates as a unit. Various other functional responsibilities may also be considered, which may also be physically attached to the computer as a unit.

Various Structural Devices

Structural devices are construction members represented in in the main casing C for housing and maintaining each of the various pieces of equipment. In the execution state, as shown in FIG. 5 and FIG. 6 (FIG. 5 being a scaled drawing), as the various construction devices, there is, at a minimum, an attached base construction body 7 which supports various measurement system devices, a couple of cases 7A and 7B which are formed using the base structure body 7, and a main casing C.

The base structure body 7 accomplishes an abbreviated U-shaped formed from a laterally extending rectangular block shaped interim body 71 and a set of standing support bodies 72 and 73 mutually standing on both sides of the interim body 71. The base structure body 7, for example, is a cast unitized product of thick metal with black coating for making marks or erasures when needed on the surface. Of course, if there is no problem in terms of the strength, or accuracy of attachment positioning, it would also be acceptable if construction provided a unitized connection accomplished by means of multiple separation and assembly.

A detailed explanation is provided next.

Figure 5:
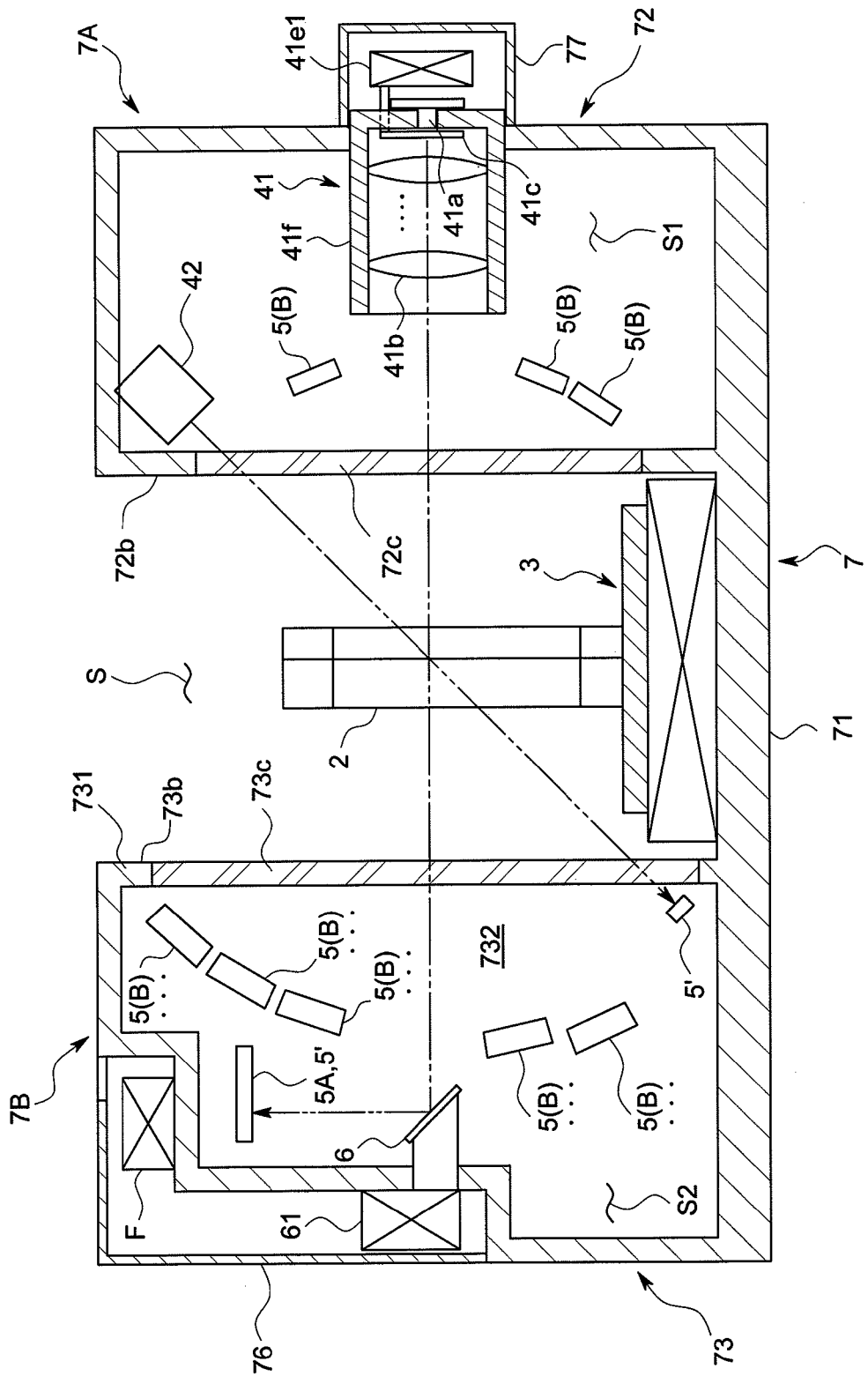
FIG. 5 is a scaled internal construction diagram showing the case, base construction body and cell storage space in the same Embodiment.
Figure 6:
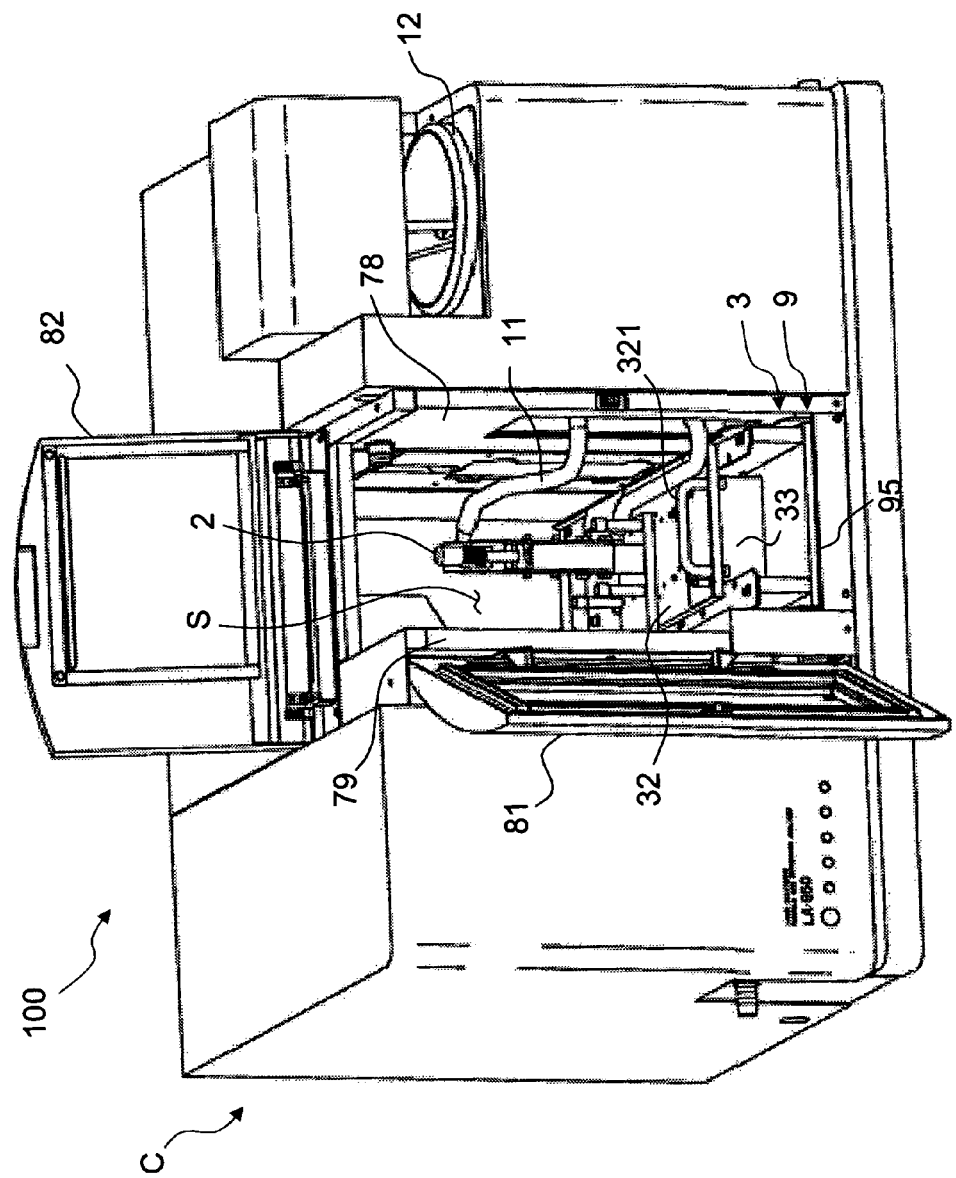
FIG. 6 is an overall oblique diagram of the main body device showing the open state of the open shut lid in the same Embodiment.

One of the standing support bodies 72, as shown in FIG. 5, is supported primarily by the laser light source unit 41 and the LED light source unit 42, and a part of the wide-angle scattered light detection group 5B. More specifically, each of the devices 41, 42, and 5B are accurately positioned by a position determining pin or the like, and inserted through an opening in the outer wall of the first storage space S1 comprising the equipment storage space provided within the standing support member 72. The opening is made so as to be blocked by a special cover or the housing body 41f of the light source unit 41 itself. By this means, on the one hand, within the first storage space S1, are arranged members which do not produce heat, such as the lighting surface side of the light sources 41a and 42a (in which the reverse lighting surface side is outside the storage space S1 attached to the base), projection light lenses 41b and 42b, a shutter 41c, and light detector 5 and the like, and power devices which generate relatively great amounts of heat, such as the shutter drive maguetic actuator 41e1, arranged outside of the first storage space S1, so as to be covered by a separate cover 77 and the like. Moreover, in lieu of attaching a cover 77, a cooling fan may also be attached, with construction which particularly cools the light source 41a with a fan, in order to prevent the temperature from increasing.

On the other hand the inside surface 72b within the first storage space S1 is a flat surface parallel to the front to rear direction, in which there is formed a penetration hole in the form of a slit, which extends so as to vertically penetrate into the first storage space S1. In the penetration hole is a tightly fitted light transmitting window 72c into which is pressed glass or a transparent resin plate, with the light produced by a semiconductor laser 41a and LED 42a being transmitted through the light transmitting window 72c, and emitted facing the standing support 73, the composition being such that the wide angle diffracted/scattered light from the cell 2 is made to be incidental.

In this manner, a first storage space S1 is formed which attaches a sealed cover or the like to one of the standing support bodies 72, structured so as to form one of the cases 7A.

Another standing support bodies 73, as shown in FIG. 5, primarily supports a narrow angle scattered light detector 5A (ring detector array), wide-angle scattered light detector 5B, transmitted light detector 5', and movable mirror 6 and the like, and is provided with a sidewall 731 which stands facing and parallel to the inside surface 72b of one of the standing support bodies 72, and a wall (rear wall) 732 which is attached perpendicular extending as a unit to the outside from a sidewall 731, forming a second storage space S2 comprising the inner device storage space.

In side wall 731 there is formed a penetration hole in the form of a slit, which extends vertically into the center. In the penetration hole is a tightly fit light transmitting window 73c into which is pressed glass or a transparent resin plate, constructed so that diffracted/scattered light irradiated onto the particles and transmitted enters the 2nd storage space S2 from the light transmitting window 73c.

In the attached wall 732 a narrow angle scattered light detector group 5A (ring detector array) is attached to one of the perpendicular surfaces (front surface), a wide-angle scattered light detection group 5B, a light transmitting detector 5', and a movable mirror 6. By this means, light detectors 5 on the perpendicular surface which includes cell 2 are scattered and arranged so as to be able to detect the light intensity of diffracted/scattered light and transmitted light introduced from the light transmitting window 73c.

By attaching a specially shaped cover to the front surface of standing support body 73, the 2nd storage space S2 is encompassed and sealed by the standing support body 73, a cover 75, and an interim body 71, so as to form the other case 7B.

Within the second storage space S2, as with the first storage space, are only arranged members which do not produce heat, such as a light detector 5 or optical components and the like, with power devices such as an actuator 61 or a cooling fanF and the like being arranged outside the outer wall of the standing support body 73, covered with a separate cover 76.

According to such construction, a space is formed which penetrates front to rear between the inside surface 72b of one of the standing support bodies 72 (one of the cases 7A) and the inside surface 73b of the other standing support body 73 (the other case 7B). However, with this embodiment, use is made of a penetrating space as the cell storage space S.

Figure 10:
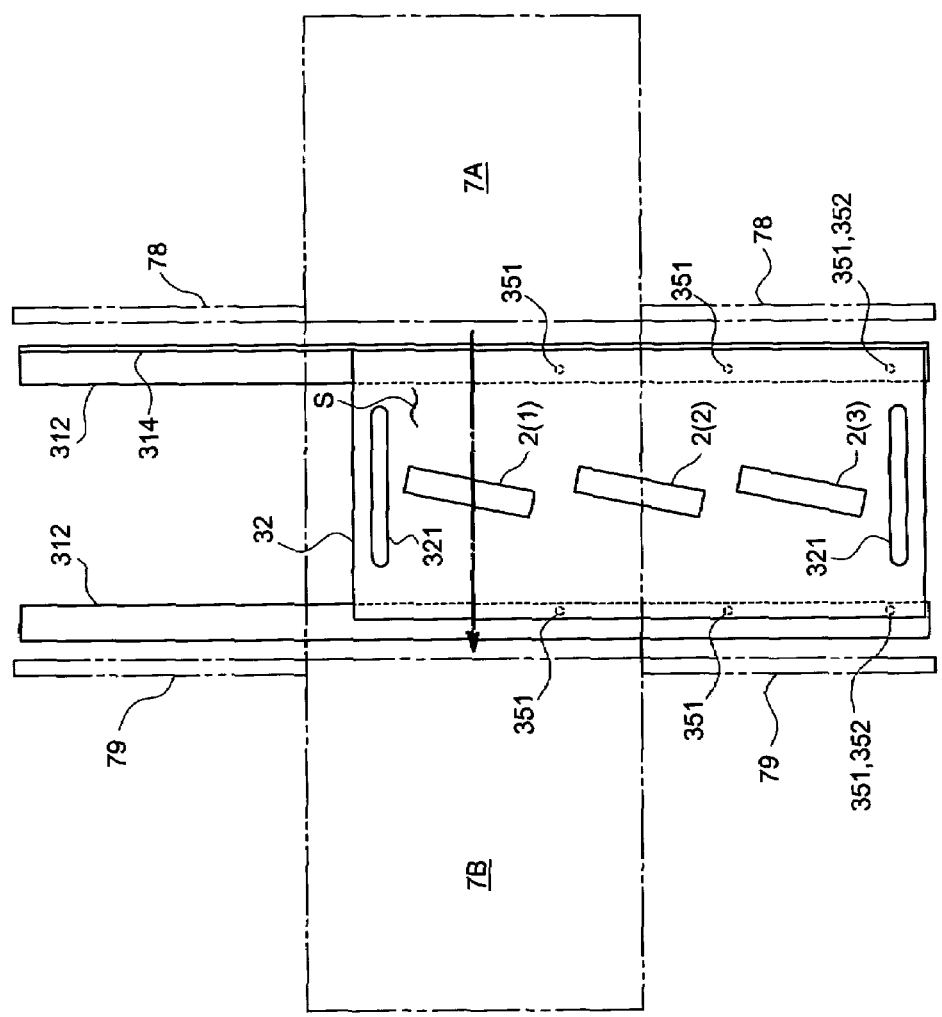
FIG. 10 is a scaled plane surface diagram showing the cell support mechanism in the same Embodiment.

More specifically, the cell storage space S is a space in which the side surfaces are made to be the inside surfaces 72b and 73b of each of the cases 7A and 7B, the bottom surface is made to be the upper surface of the interim body 71, and the aperture is formed to open front to rear and upwardly. In the embodiment, as shown in FIG. 6 and FIG. 10, from the front and rear borders of the inside surfaces 72b and 73b, further to the front and rear are extended finishing walls 78 and 79. In extending the cell storage space S front to rear, by means of the main casing C, the front and rear surfaces as well as the upper surface of the cell storage space S are covered with a seal member (such as for example, an epoxy sealer or a packing member), by which the cell storage space S is tightly sealed.

Figure 7:
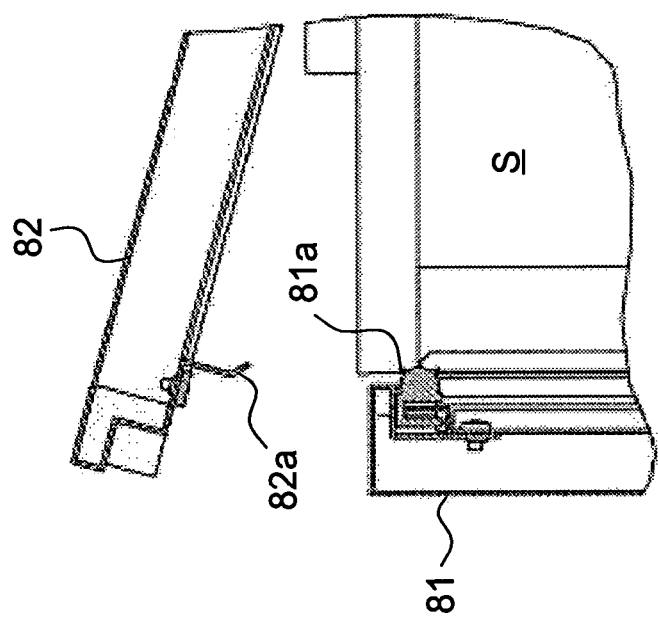
FIG. 7 is a partial cross-sectional diagram showing the seal construction of an open shut lid in the same Embodiment.
Figure 8:
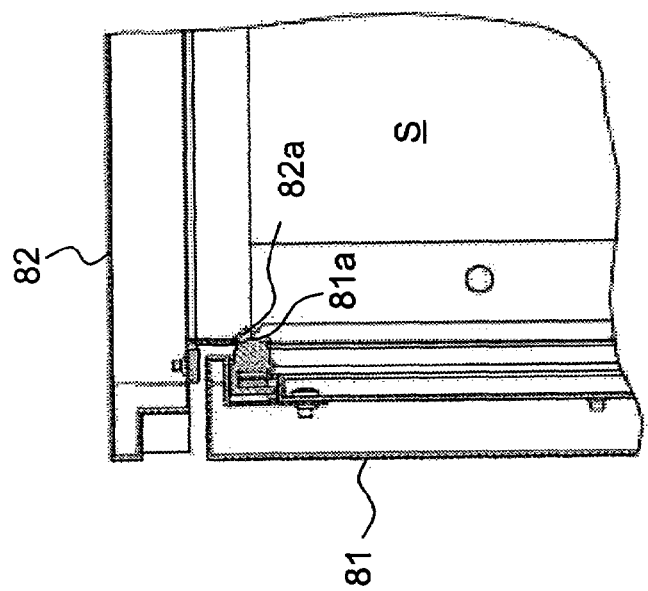
FIG. 8 is a partial cross-sectional diagram showing the seal construction of an open shut lid in the same Embodiment.

Furthermore, in the main casing C, in parts corresponding to the front surface of the cell storage space S, an open shut lid is attached, rotatably supported so as to laterally open by means of a vertical axis, and constructed so that the front surface can be open and shut. In addition to attaching an open shut lid 82 the front half of the upper surface of which opens upwardly and in which the rear end is rotatably supported by a horizontal axis, it is constructed so that the front half of the upper surface can be open and shut. In the closed state, open shut lids 81 and 82 are sealed by peripheral packing, by which the cell storage space S is substantially sealed tight. Moreover, between the front end of the open shut lid 82 and the upper end of the open shut lid 81, as shown in FIG. 7 and FIG. 8, in addition to attaching a contact surface 82a inclined at roughly 45° when viewed from the direction of one side (in this case the upper open shut lid) of an open shut lid, in the other direction (in this the front open shut lid), in the closed state, an elastic packing member 81a is attached close to the contact surface 82a. With such sealed construction of this part, by making the seal surface (the contact surface 82a and the contact part of the packing member 81a) to face an inclination relative to the direction of opening and shutting, and when either of the open shut lids 81 or 82 are open and shut, sliding with extended rubbing between the packing member 81a and the contact surface 82a is prevented, suppressing abrasion related loss.

In addition, in the cell storage space S, other than multiple cells 2, the cell 2 is supported so as to be forwardly and retractably movable in the rearward direction (the pass-through direction of the cell storage space S), and any single cell 2 can attach a cell support mechanism 3 by which it is selectively positioned in the light irradiation position in which light is irradiated from the light source, and a tray 9 which mounts on the cell support mechanism 3.

Multiple cells 2, as described above, are of differing types (for example the wet format flow cell, the wet format batch cell, and the dry batch cell).

Cell support mechanism 3 is provided by a rail member 31 which stretches forward and backward, and a cell mounting member 32 which mounts each cell 2, a narrow support body 33, and an elastic member 34 which is arranged between the cell mounting member 32 and the narrow support 33. Construction is such that, by the pulling strength of the elastic member 34, the cell mounting member 32 advances forward and retreats backward along the rail member 31, while the rail member 31 is interposed by cell mounting member 32 and the narrow body 33.

Figure 9:
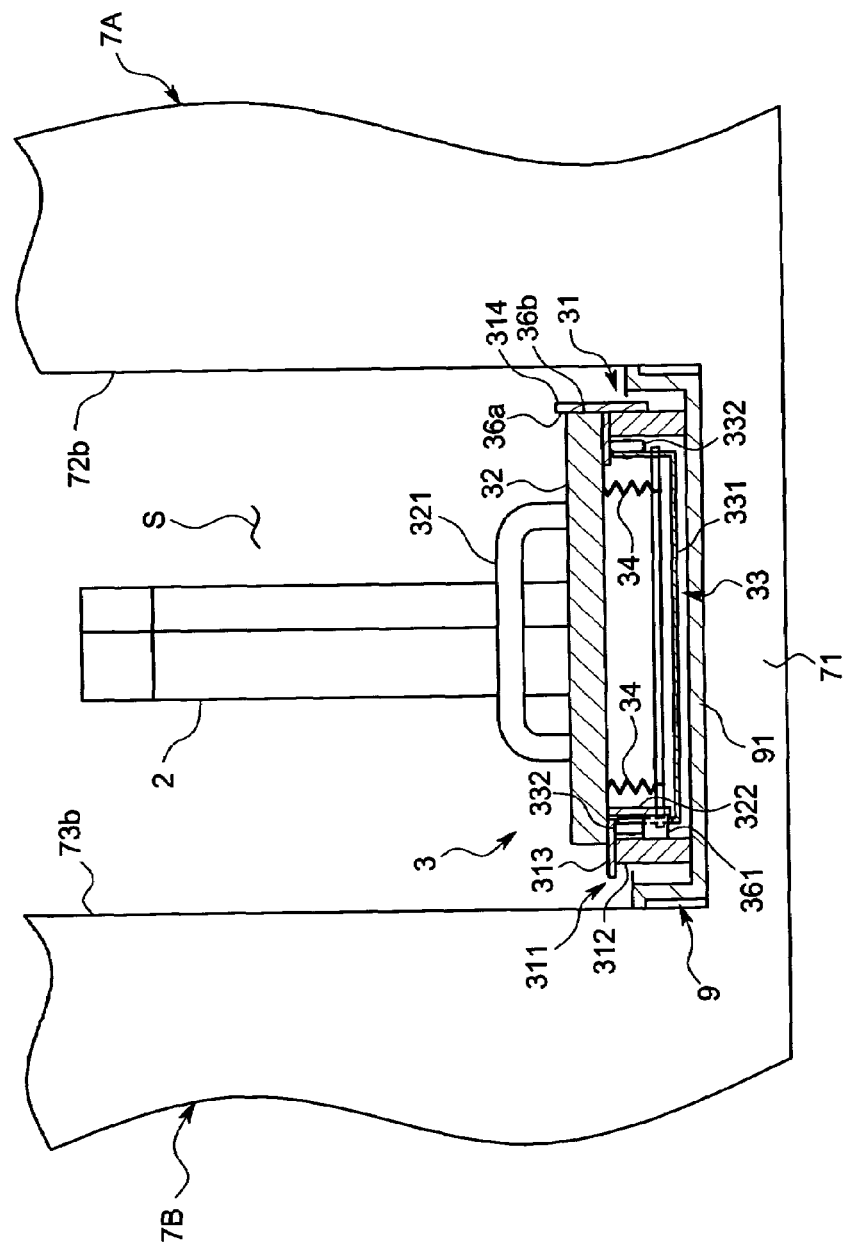
FIG. 9 is a front surface scaled diagram showing the cell support mechanism in the same Embodiment.

Specifically, the rail member 31 is provided with a set of parallel rail elements 311. Each rail element 311 is formed from a standing plate 312 and a horizontal plate 313 attached to the upper surface of the standing plate 312, which stands vertically from the bottom plate 91 of the tray 9 described hereafter, see FIG. 9.

The cell mounting member 32 is formed in the shape of a rectangular plate, and is arranged on the horizontal plate 313 of the rail member 31. Also, each cell 2 is supported in a row on the upper surface of the cell mounting member 32, in the forward to rearward direction (direction of advancement and retreat). Each cell 2 is directly supported and inclined relative to the direction of light radiation, and is removably attached to the cell mounting member 32 through an unshown cell holder. This reduces the influence of reflection on the surface of cell 2. In addition, a grasp 321 is at a minimum attached to the cell mounting member 32 for convenience in movement.

A narrow holding body 33 is provided with a narrow holding main body 331 of a box shape the opening to which is on the upper surface, and disc rotating bodies 332 which are rotatably attached through a horizontal axis extending laterally (in the cell advancement and retreat direction and intersecting direction) on the outside of the upper end of the side plate of the narrow holding main body 331. Rotating bodies 332 are respectively attached to the left and right of the front and rear sections, and arranged to be lower than the horizontal plate 313 of the rail member 31.

Elastic member 34 is a pull coil spring attached between the narrow support body 33 and the cell mounting member 32, and in addition to being attached to the lower end of the lateral bridging axis which bridges the side plates of the narrow support body 33, it's upper end is attached to the engagement stop attached to the cell mounting member 32, and vertically pulls the support body 33 and the cell mounting member 32.

In this embodiment, 2 pull coil springs are attached to the rear, and 2 are attached to the front. The rear pull coil springs 34 are arranged on the inner side of the rear rotating body 332, and in roughly the same position front to rear. In addition, the front pull coil spring 34 is arranged more to the front side than the rotating body 332. Also, through the pulling force of these elastic members 34, the first contact surface attached to the cell mounting member 32 (specifically the lower surface of the side margin) and the second contact surface (specifically the external peripheral surface of the rotating body 332) make movable pressure contact while being vertically interspersed between each of the horizontal plates 313 of the rail member 31.

In addition, the cell support mechanism 3 is provided with a position determining mechanism 35 which stipulates the light irradiation position of each cell 2. The position determining mechanism 35 is provided with multiple engagement holes 351 on one side (in this instance the horizontal plate 313 of the rail member 31) of the rail member 31 and the cell mounting member 32, and an engagement pin 352 which is attached to the other side (in this instance the lower surface of the cell mounting member 32). By noiselessly engaging any of the engagement pins 352 with an engagement hole 351, any single cell 2 can be selectively positioned in the light irradiation position. Moreover, movement of the cell mounting member 32 can be accomplished in an incline by moving the grasp 321 on the front side of the cell mounting member 32 upwardly, releasing the engagement between the engagement hole 351 and the engagement pin 352, see FIGS. 10 and 11.

Furthermore, the cell support mechanism 3 is provided with a lateral movement suppression mechanism 36 which prevents lateral movement of the cell mounting member 32. The lateral movement suppression mechanism 36 suppresses lateral movement of the cell mounting member 32 by pressing the covered guide in the surface 36b (specifically the outside surface of one direction of the cell mounting member 32) attached to the cell mounting member 32 in the guide surface 36a (specifically the inner side surface of plate 314 standing from the outside surface of the rail element 311) which is parallel to the forward and rearward direction (cell advancement and retreat direction) provided to the rail member 31. Owing to this, between the cell mounting member 32 and the rail 31 is attached a second elastic member 361 which operates a lateral elastic recovery force. This second elastic member is a plate spring attached to the support plate 322 vertical from the lower surface of the side margin of, for example, the cell mounting member 32. The plate spring 361 pressures the inner surface of the standing plate 312 of the other direction in the rail member 31, and with a reverse force presses the outside surface 36b of a cell mounting member 32 to the inner side surface 36a of the hit plate 314.

With such construction, even while making it possible for multiple cells 2 to switch the direction of advancement and retreat, vertical and lateral movement of the cell mounting member 32 is suppressed at the time of measurement, with measurement precision and while accurately accomplishing position determination.

Figure 11:
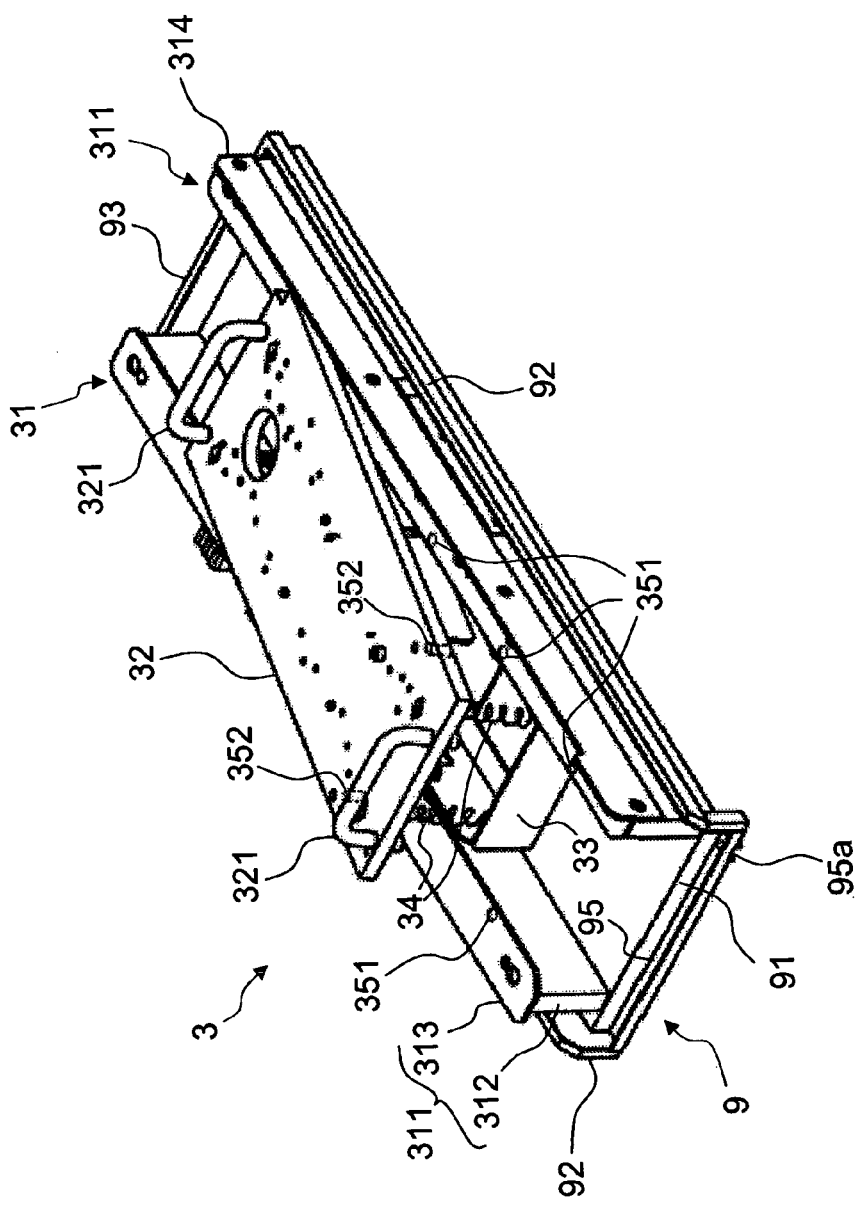
FIG. 11 is an oblique diagram viewed from a specific angle showing the cell support mechanism in the same Embodiment.

The applied cell support mechanism 3 is mountingly fixed on a tray 9 secured to the upper surface of the interim body 71. The tray 9, as shown in FIG. 11, is provided with a box which is provided with a bottom plate 91 which mounts a cell support mechanism 3, lateral side plates 92, a rear plate 93, and a front surface opening, the height of which is low, with a lateral conduit 95 being provided at the lower part of the end border. The tray 9 receives the sample liquid spilled by mistake at the time of exchanging the cell 2, and the sample liquid spilled onto the tray 9, as shown in the scaled diagram 12 is transferred to the conduit 95, and is expelled from the exit 95a fixed to its end, and is then led to a circulation tray T and finally expelled to the outside from the drain of the recirculation tray T provided to receive the spilled sample liquid or dispersion medium. Of course, the tray 9 formed into a box has an opening only on it's upper surface, and discharging liquid sample by using a hose or pipe from the bottom plate or using another discharge system may also be considered.

Figure 12:
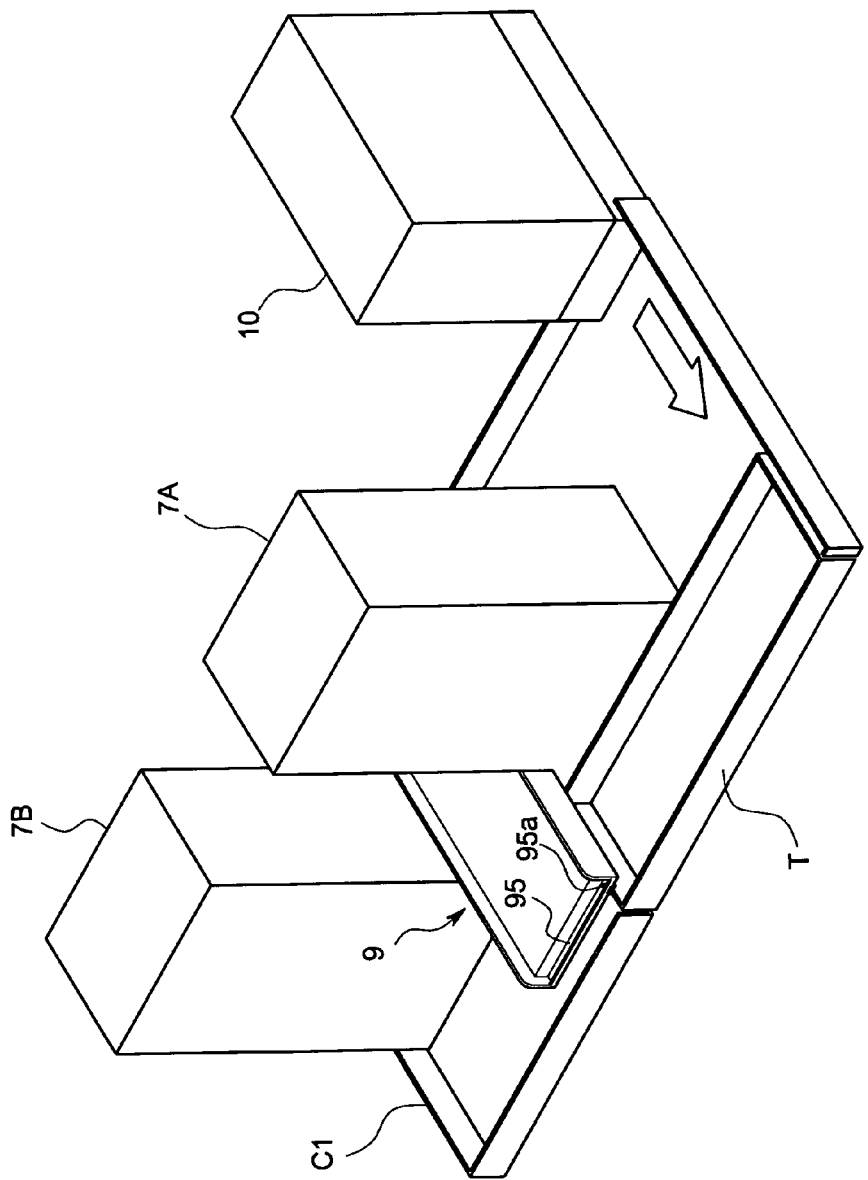
FIG. 12 is a scaled oblique diagram showing the attachment of conduit construction and an electricity source rack in the same Embodiment.
Figure 13:
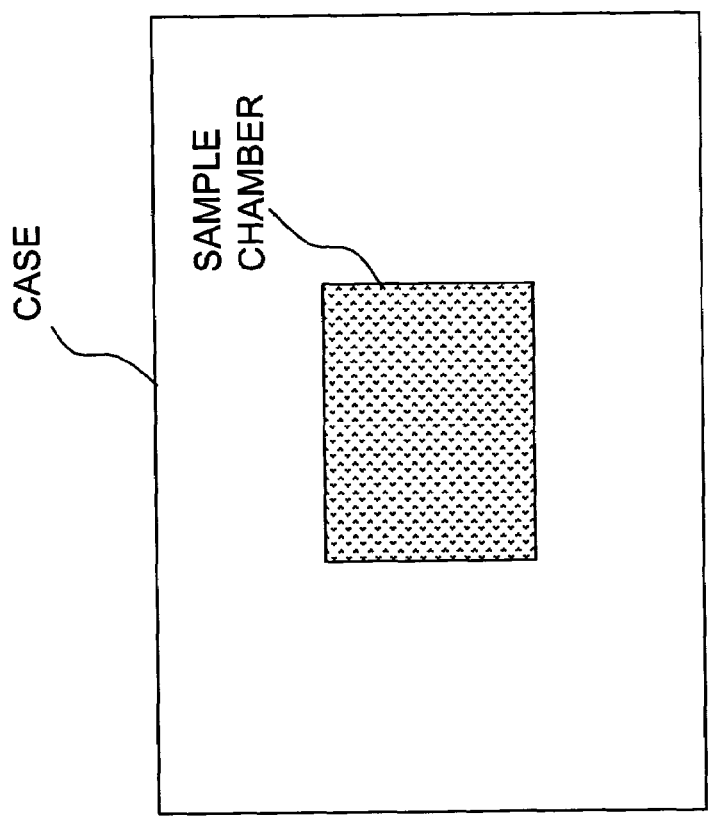
FIG. 13 is a plane surface diagram showing the arrangement of a scaled conventional device.

Lastly, a simple explanation is provided with regard to the main casing C. Main casing C, with the exception of information controller 62, forms a device body which stores all of the devices. As shown in FIG. 1 and FIG. 6, a center space is provided roughly formed as rectanglular parallel piped. In other words, in the main casing C, other than housing the base construction body 7 or the cases 7A and 7B formed by its use, in a separate space is stored electric source unit 10 and various circulation system devices. Moreover, as shown in scaled fashion in FIG. 12, electric power unit 10 is attached to the bottom plate C1 of the main casing C in a manner so as to be slidingly removable.

Effect of the Present Embodiment

The present embodiment is provided with equipment storage spaces S1 and S2 in which are stored at least one of light sources 41a and 42a, a light detector 5, and optical devices 41b, 42b and 6 and the like, and which have sealed construction in which the user can accomplish airtight separation between the open and shut cell storage spaces S. By preventing temperature changes or counter airflow, and abnormal mixing, the internal environment is stabilized, making it possible to take measurements with a high level of stability and replication, which is long-term maintenance free. In addition, the cell storage space S also can be said to be open and shuttable, and in a state in which the open shut lids 81 and 82 are closed, since adequate air tightness is accomplished by means of sealing members of packing and the like, it is endowed with measurement stability.

In addition, since the device storage space S1 and S2 are respectively divided and formed in each of the laterally divided cases 7A and 7B, in comparison to the case in which one large device storage space is formed, stabilizing or sealing the internal environment can be easily accomplished. In addition, forming a space between cases 7A and 7B has the basic construction of an aperture penetrating from front to rear and upwardly as well, in which embodiment the aperture surface is only covered by the main casing C comprising an externally attached mechanism. By only changing the part which attaches open shut lids 81 and 82 and the main casing C, the opening part can be simply changed for operating purposes without changing the basic construction. Furthermore by means of the packing seal attached between the open shut lids 81 and 82 and the border of their opening, an adequate seal can be assured at the time of measuring the cell storage space S.

Furthermore, along with providing each of the cases 7A and 7B with sealed construction, by putting generating actuators or power devices such as electric power sources outside of each of the cases 7A and 7B, various measurement system devices can be arranged in a thermally separated room. By so doing, the environment of the various measurement system devices can be maintained and fixed to the extent possible, with improved measurement precision and stability.

In addition, with construction in which the cell storage space S is interspersed in the manner of the present embodiment, cases 7A and 7B can be separated, and ordinarily if there is position slippage between the cases 7A and 7B, there is also slippage in the position relationship of the apportioned storage of various measurement system devices. Depending upon the situation, position slippage will not be able to be absorbed in the final optical adjustment stage, and it may also be possible to perform re-assembly, in which a unit base construction body 7 is attached, and in addition to attaching various measurement system devices, since each of the cases 7A and 7B will be formed using the case construction 7, positional precision will be assured in the assembly of the various measurement system devices.

Since by forming the cell storage space S between the cases 7A and 7B, operation becomes possible both upwardly and forward relative to the cell storage space S, in comparison with the fact that heretofore operation was only possible upwardly, there will be greatly improved operability within the cell housing S.

Furthermore, since forming a cell storage space on the outside of the cases 7A and 7B is an entirely new concept, separation between the cell storage space S and the cases 7A and 7B can be easily maintained.

For example, the introduction of the entirely new measurement format of spraying the cell storage space S and measuring the sprayed granule diameter can be easily accomplished. In addition, since the two cases 7A and 7B are separated, changes in their positional arrangement and the like enable various variations in the design stage, valuable for future development.

Furthermore, since activating the pass-through nature of the cell storage space S, and constructing it so that multiple cells 2 can be made movable provided in the pass-through direction, makes it possible for 1 among many cells 2 to be selectively positioned in the light irradiation position of light irradiated from a light source, further improved operability with the cell storage space S can be achieved by simply switching to another measurement format by only sliding the cell 2, without the need for its removal and exchange.

Examples of Modification

The present invention is not limited to Embodiment 1.

For example, the cases may also be arranged front to rear, and depending upon the circumstance may also be arranged vertically. In addition, the open shut lids 81 and 82 need not be separate, but may also form a single unit.

In addition, the interim body in the base construction body may be constructed to be the rear plate or upper plate, rather than the bottom plate. In this case, the standing support body can be stood facing to the front or downward.

Furthermore, the light detector in the embodiment is separately arranged in the vertical surface, however construction in which the light detector is arranged within a horizontal surface is also possible.

(2) Second Embodiment

An explanation of an embodiment of the invention is provided hereafter with reference to the drawings. Moreover, there are some members having the same labels as those cited in Embodiment 1, however there are some which are also fundamentally not the same.

Figure 14:
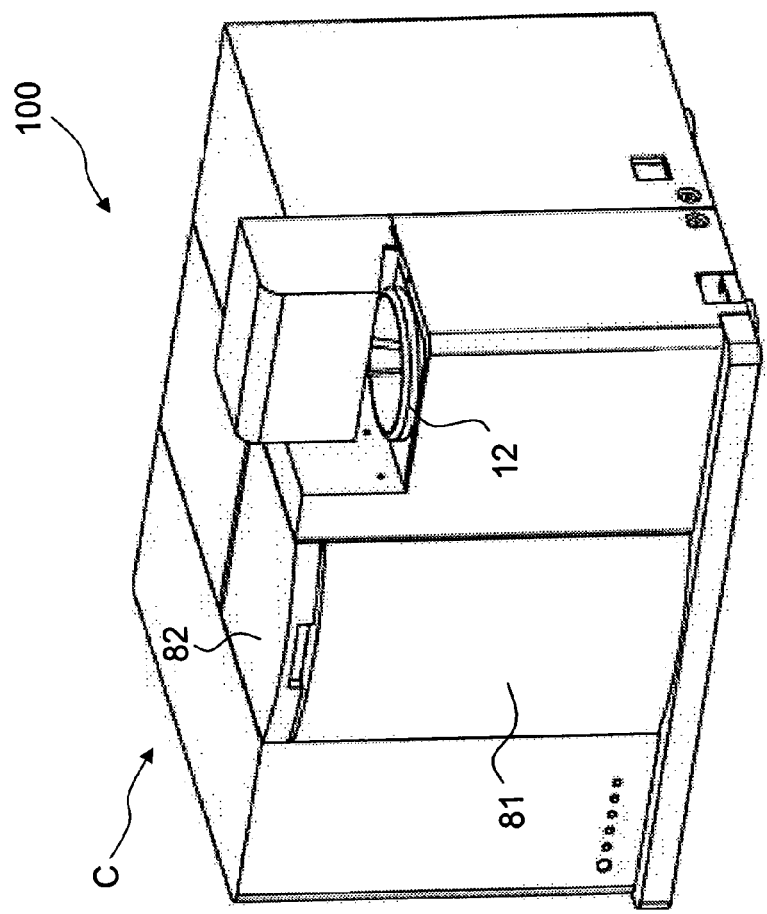
FIG. 14 is an overall oblique diagram showing the main body of a particle size distribution analyzer in a second Embodiment of the present invention.
Figure 15:
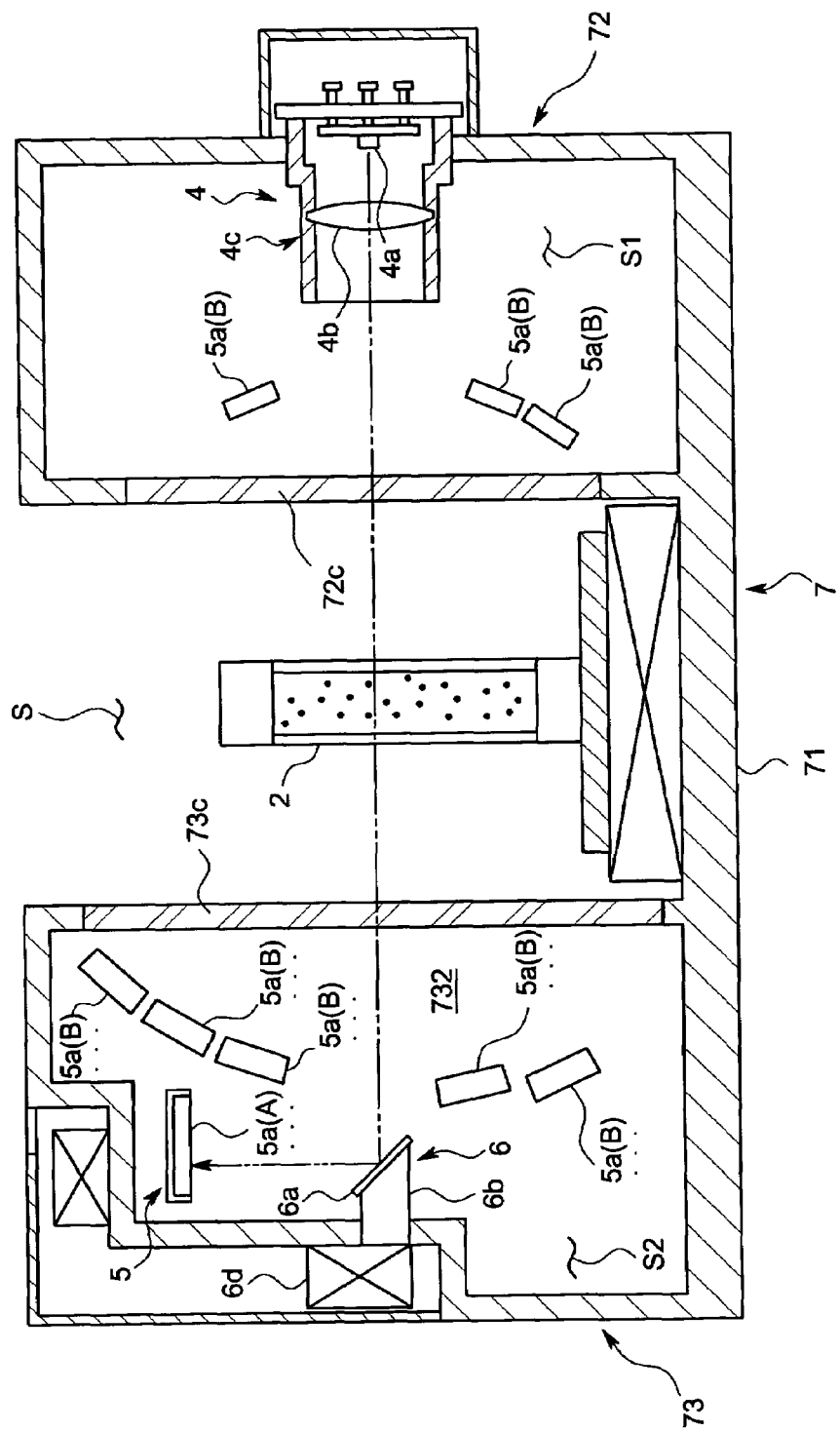
FIG. 15 is a scaled internal construction diagram showing the base construction body and storage space in the same Embodiment.

The particle size distribution analyzer 100 relating to the present embodiment, which, as shown in the overall external view of FIG. 14, detects a diffracted scattered pattern (diffracted/scattered light intensity angle distribution) of diffracted/scattered light at the time of irradiating light onto the particles which is the subject of measurement, and executes Fourier exchange computations based on the MIE dispersion theory from the diffracted scattered pattern, and measures the particle size distribution, and as shown in the primary construction scaled diagram, with the exception of the computer and the like shown in FIG. 15, it is minimally provided with a base construction body 7, a light source 4 supported in the base construction body, a cell 2, and various measurement systems devices such as a detector 5 and the like.

The base construction body 7, as shown in FIG. 15, is provided with a laterally extending interim body 71 of a rectangular block (thick plate shape), and forms an abbreviated U-shaped formed from a set of standing support bodies 72 and 73 which are mutually separated, and standing as a unit on each sides of the interim body 71. Also, to one of the standing support bodies 72 is attached a first storage space S1, in which the primary measurement system is a device on the light source side, and in addition to providing support storage, at the other end of the standing support body 73 there is an attached second storage section S2, in which the measurement system devices on the optical detection side are made to be primary, and are supported and stored.

Furthermore, in the cell storage space S formed between the standing support bodies 72 and 73, the cell 2 is stored. Moreover, labels 72c and 73c represent transmitting windows for transmitting light from a light source and diffracted/scattered light. Base construction body 7 is a cast unit type product of a thick metal which executes a light coating device which can make marks or erasures in necessary locations, as needed. If there is no problem in terms of intensity or positioning accuracy, they may be multiply separated or assembled as a unit.

In the same manner, as shown in FIG. 15, as the various measurement system devices, attachment may be made of a transparent cell 2 which stores the particles dispersed in the dispersion medium, and a light source 4 which irradiates light onto the particles in the transparent cell 2, and multiple light detectors 5 separately arranged to output the intensity of diffracted/scattered light produced by the irradiation of light, and other optical devices or slits and the like.

An explanation is provided concerning each component.

Cell 2 is for example, of resin construction, and in FIG. 15 shows a wet format batch. Other than that, construction may also be provided to switch to use cells 2 or the like by supporting and performing measurements of multiple cells of differing types (for example wet flow cells, wet batch cells, and dry batch cells) made movable by means of an unshown cell support mechanism.

The light source 4a is a semiconductor laser which produces, for example, red light. However, use may also be made of other light sources, such as an LED and the like, and use may also be made of multiple types of light sources of different wavelengths. For example, by using multiple light sources of different wavelengths, the measurable range of the granules can be broadened without any loss of precision.

Construction is such that, on the light emission side of light source 4a is arranged a projection lens 4b. Also, light which broadens as it is put out from the light source 4a is refracted by the projection lens 4b, and is irradiated onto the cell 2 as converging light.

Figure 16:
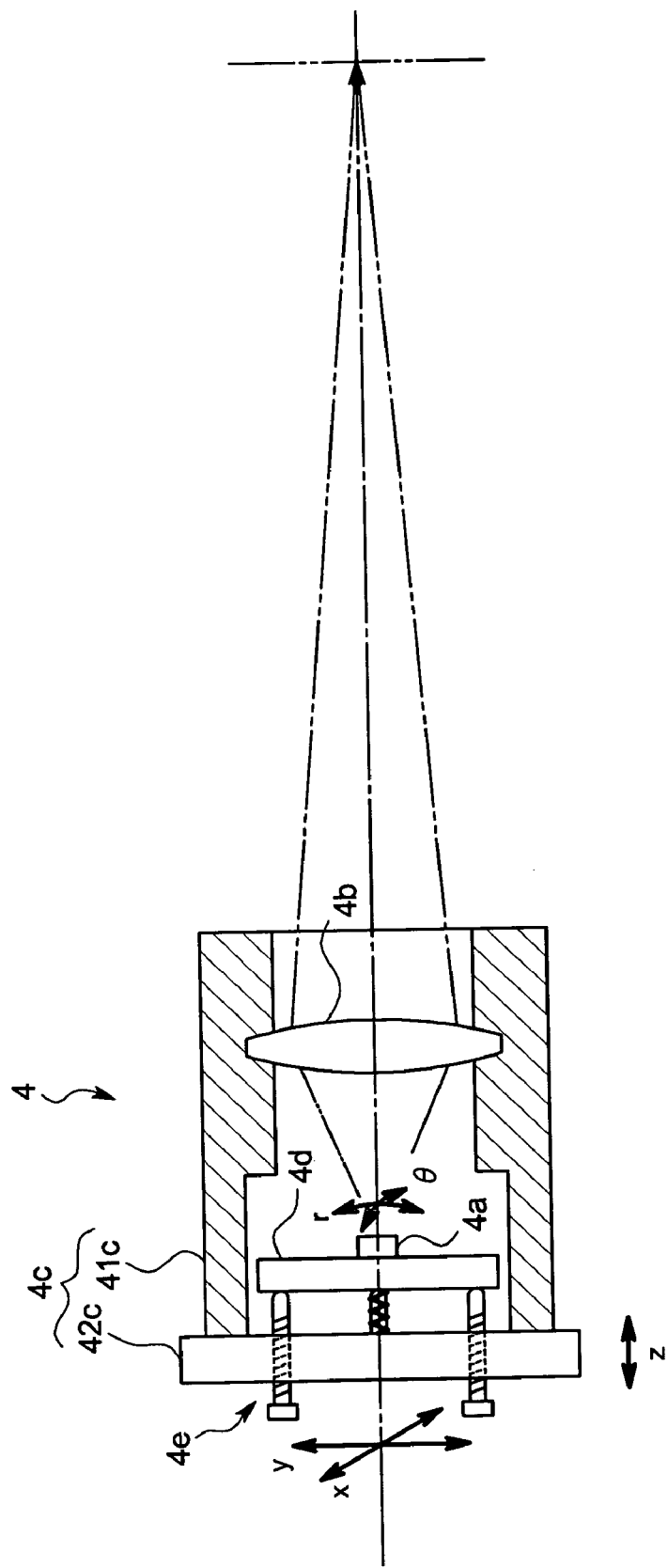
FIG. 16 is a scaled vertical cross-sectional diagram showing a light source unit in the same Embodiment.

Furthermore, in the present embodiment, as is particularly shown in FIG. 16, the light source 4a and the projection lens 4b are maintained as a fixed unit by the support body 4c, forming a light source unit 4.

The support body 4c is provided, for example, with a lens barrel 41c which supports the projection lens 4b, and a base member 42c which is attached so as to cover the bottom of the lens barrel 41c, and by means of construction in which either of the lens barrel 41c or the base member 42c is engaged to the base construction body 7 by means of an engagement hole and a position determining engagement pin, it can be noiselessly attached (accurately with only slight slippage in terms of mechanical precision). Also, to the surface of the lens barrel 41c side in the base member 42c is attached a substrate 4d which mounts a semiconductor laser 4a.

The base 42c, relative to lens barrel 41c is position adjustably attached, advancing and retreating in the triaxial direction xyz, and the substrate 4d is attached to be inclinably adjustable in the bi-directional rθ. The advancing and retreating mechanism and the inclining movement mechanism realizes a 3 support mechanism by means of a screw transport mechanism or movable screw, and serves the role of an optical track adjustment mechanism 4e. Also, by means of the optical track adjustment mechanism 4e, the relative positional relationship between the semiconductor laser 4a and the light projection lens 4b can be adjusted freely by the 5 degrees of xyzrθ. As a result, from the semiconductor laser 4a through the light projection lens 4b, adjustment can be accomplished of the light track emitted to the outside.

Light detector 5a utilizes a photodiode and the like, and outputs a strong electrical signal (light strength signal) corresponding to the intensity of the received light. The total number of light detectors 5 is, for example, between 90-100 units, scattered and arranged above the vertical surface, including the cell 2 and its periphery. In particular, in the embodiment, as shown in FIG. 15, the detectors 5a are classified into narrow scattered light detectors 5a(A) for precisely detecting the angle of the diffracted/scattered light having a small angle of less than a fixed angle, and with angles which are wider, and wide-angle scattered light detectors 5a(B) for detecting diffracted/scattered light in the side direction and rearward direction from the front direction.

Figure 17:
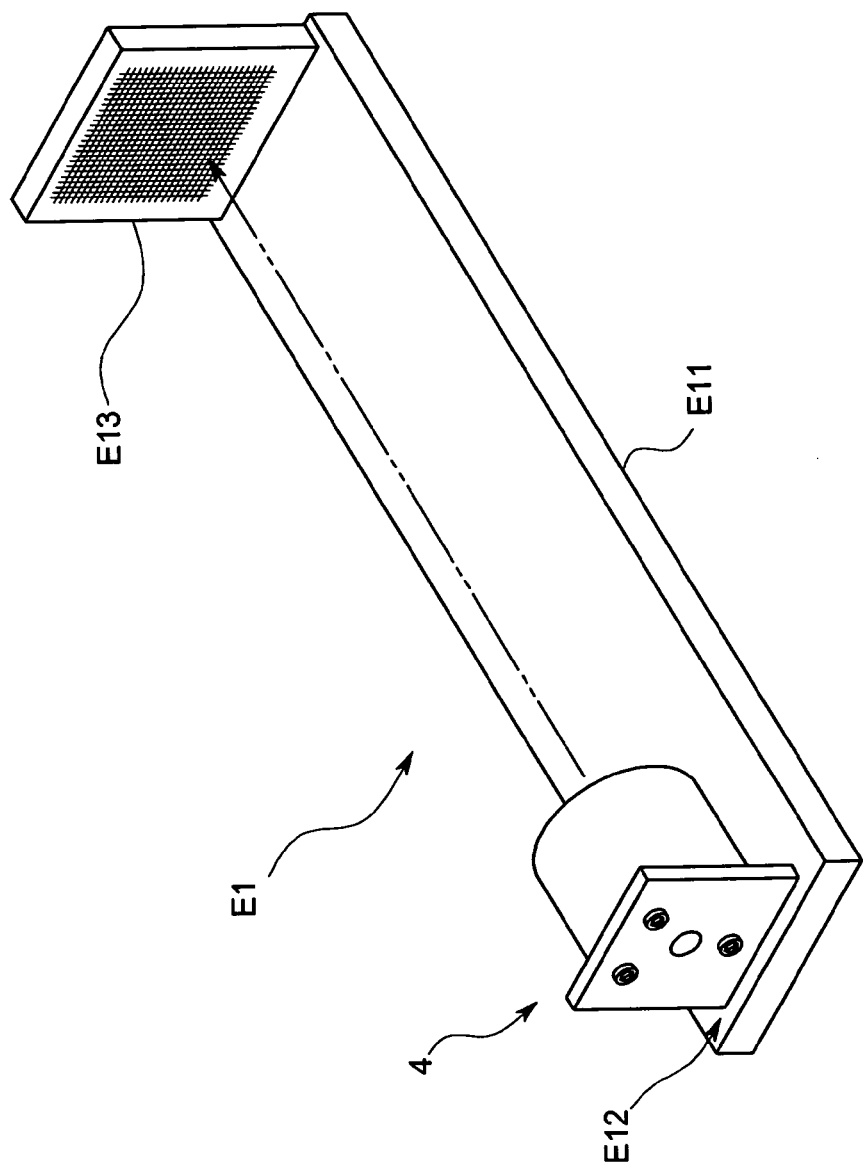
FIG. 17 is a scaled oblique diagram showing a light track confirmation jig in the same Embodiment.

Also, in the present embodiment, as shown in FIG. 15 and FIG. 17, multiple narrow angle scattered light detectors 5a(A) are arranged in a circular shape with an extremely narrow width on the substrate 5b, making a ring detector array, and by providing a substrate 5b, and a second support body 5c which supports the substrate 5b a detection position adjustment mechanism (not shown) for adjusting the position of the substrate 5c (detector 5a(A)) relative to the second support body 5c, and unitized optical detector unit 5 can be accomplished.

The detector position adjustment mechanism is not shown in detail. However, its purpose is to adjust the position relating to the three directions xyz of the narrow angle scattered light detector 5a(A) relative to the second support body 5c, realized using a spring transport mechanism and the like. Also, the 2nd maintenance body 5c, by the engagement position determination construction of an engagement hole and the pin with which it is engaged is noiselessly attached (accurately, with slippage of only the mechanical difference).

Furthermore, with the present embodiment, as shown in FIG. 15, the light path length to the narrow angle scattered light detector 5a(A) from the light source 4a is extended, and in order to have an abbreviated space, the diffracted/scattered light is led to the narrow angle scattered light detector 5a(A) through mirror 6a.

Also, by unitizing the mirror 6a and the third support body (not shown) which supports the mirror 6a, and the mirror posture adjustment mechanism 6b for adjusting the posture of mirror 6a relative to the third support body, the mirror unit 6 is formed, and is supported in the base construction body 7.

The mirror posture adjustment mechanism 6b is not shown in detail in the drawing. However, in order to adjust the mirror posture relative to the third support body, the mirror posture adjustment mechanism 6b can be automatically operated by the mirror drive mechanism 6d. In addition, the third support body is noiselessly attached by the engagement position determination construction of the engagement hole and the pin with which it is engaged (accurately and slipping only by the mechanical difference).

Next, an explanation is provided relating to the assembly method of various measurement system devices relating to an embodiment having this type of construction.

First of all, an adjustment is made so that slippage relative to the lens barrel 41c of the light track path emitted from the light source unit 4 is adjusted to within permissible limits. At this time, use is made of the optical track confirmation jig E1. The optical track confirmation jig E1, as shown in FIG. 17, is provided with, for example, a base table E11, a light source unit fitted unit E12 attached to one end of the base table E11, and a standard light detector E13 of the surface type of an attached CCD and the like, positionally established at the other end of the base table E11.

Accurate position determination can be provided to the light source unit attachment component E12 by providing the light source unit 4 (more specifically a lens barrel 41c and base member 42c) with a pin engagement and the like. In this manner, if light is emitted from the light source unit 4 attached to a base table E11, and the light is led to the standard light detector E13, the question of within what parameters the output light will be positionally irradiated, in other words the light track, will be accurately understood. In order for this to be determined within specified parameters, the light tracking adjustment mechanism 4e is operated and adjustment is made. By so doing, tracking (specifically tracking relative to the lens barrel 41c and the base member 42c) of the light emitted from the light source unit 4 will be fixed to within some standard.

Figure 18:
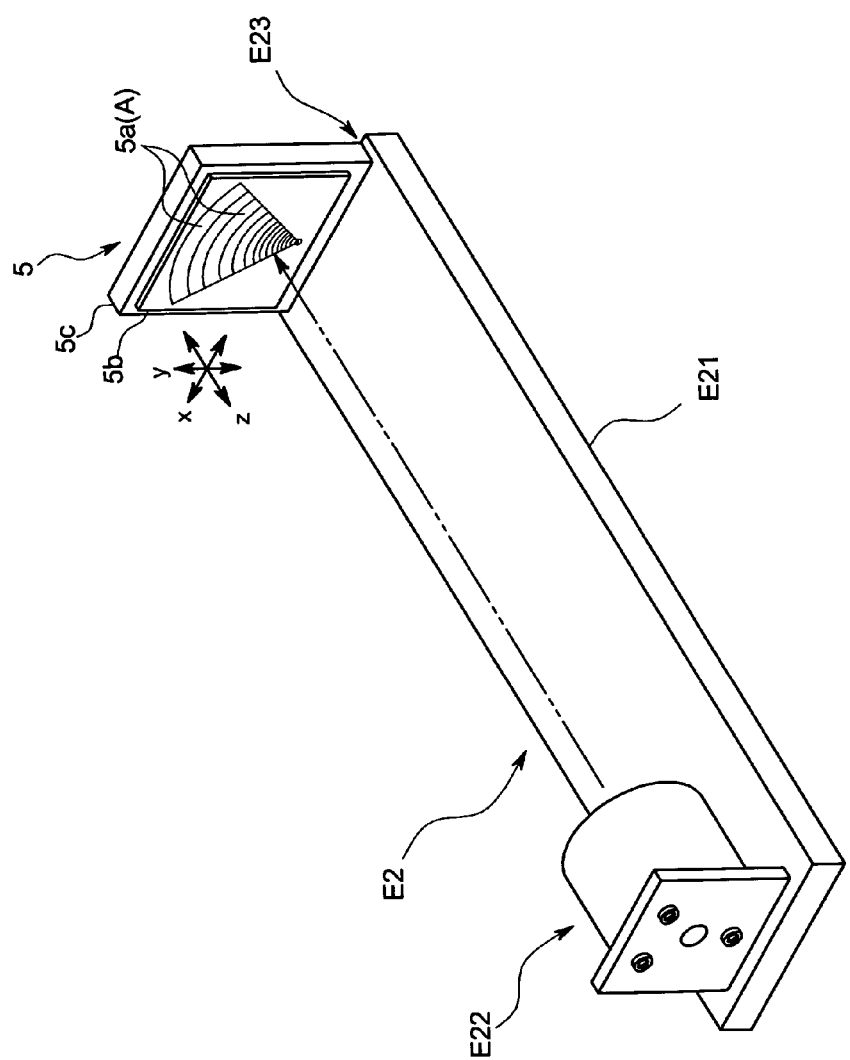
FIG. 18 is a scaled oblique diagram showing a detector position confirmation jig in the same Embodiment.

On the one hand, adjustment is made of the position relative to the second maintenance body 5c of the light detector 5a(A). At this time, use is made of the detector position confirmation jig E2. The detector position confirmation jig E2, as shown in FIG. 18, is provided with a base table E21, and a standard light source E22 positionally determined and attached to one end of the base table E21, and a detector unit attached component E23 which is attached to the other end of the base table E21.

In the detector unit attachment component E23, the detection unit 5 (more specifically the second support body 5b) can be accurately and positionally determined and attached by the engagement of a pin and the like. In this manner, if standard light is irradiated from the standard light source E22 to the detector unit 5 attached to the base table E21, since it will be known from the output of the light detector 5a(A) which detector 5a(A) is reached by the standard light, or if it is not reached, in order to determine within what specified parameters the standard light will be able to reach (specifically so as to reach the transmitted light detector in the center of the arc), the detector position adjustment mechanism is operated, and adjustment is made, by which means the position of the light detector in the detector unit 5 will be fixed within the standards.

The same is true with regard to mirror unit 6 as well. Although not shown in the drawing, the posture of the mirror 6a relating to the third maintenance body 3 is adjusted using a mirror posture confirmation jig. By so doing, the posture of the mirror 6a in the mirror unit 6 can be fixed within the standards.

Finally, a light source unit 4, a detection unit 5 and a mirror unit 6 which have been thus adjusted and brought to within standards are attached in a specified position, using position determining construction in the base construction body 7. Moreover, other unshown slits or other optical detection devices (such as a wide angle diffracted/scattered light detector 5(B) and the like) can also be provided with position determination in the specified position of base construction body 7.

By so doing, relative to the base construction body 7, the support body 4c (specifically the lens barrel 41c or the base member 42c) of the light source unit 4, the 2nd support body 5b of the detector unit 5 and the 3rd support body of the mirror unit 6 can be position determined by pin engagement and the like. Furthermore, in the light source unit 4, the support body 4c (specifically the lens barrel 41c or the base member 42c) and the light tracking are adjusted using the adjustment jig E1. In addition, with the detection unit 5 as well, the 2nd support body 5b and light detector 5a(A) are adjusted in the same manner, and further, in the mirror unit 6 as well, since adjustment of the 3rd support body and the mirror 6a will have already been performed, by attaching the light source unit 4, the detector 5 and the mirror unit 6 to the base construction body 7, the light tracking and light detection position can be made to have the desired corresponding relationship within the limits of mechanical precision.

In addition, finally, as the light axis of the light detector 5a(A) will be positioned in the center, while monitoring the output value of the light detector 5a(A), posturing of the mirror 6a can be automatically performed by the mirror drive mechanism 6d. However, precise position determination is done at the time of initial attachment, and since there is only a slight need to move the mirror 6a to correct mechanical differences, control at this time can be easily accomplished.

In this manner, while conventionally bench mounting was accomplished one by one of each of the optical system components, using the phenomenon of interference light which was difficult to handle, with the present embodiment, without accomplishing position determination, since a pre-adjusted light source unit 4, detector unit 5, and mirror unit 6 can be simply attached to a base construction 7 which has position determining construction, anyone can simply and accurately assemble the measurement system device in a short period of time.

Furthermore conventionally, since slippage between the position and posture of the light source and light detector is allowed, if the light source and detector are changed as part of maintenance, differences between the position and posture is generated to the extent that they cannot be automatically absorbed by the mirror, requiring re-adjustment of the entire optical system. However, according to the embodiment, since each of the units 4-6 are pre-adjusted by an attached adjustment mechanism to within specified standards, and since each of the units 4-6 can be positionally attached to a unitized base construction body 7, automatic adjustment can be accurately executed within parameters by the mirror unit 6, and, for example, during maintenance, the great operational burden of performing optical re-adjustment after changing parts, as was done under the prior art, can reduced, by only changing the units 4-6, Moreover, the present invention is not limited to this embodiment.

For example, the adjustment mechanism of xyzrθ may also be attached on the detector side, simplifying the adjustment mechanism on the light source side. In addition, the adjustment mechanism on the detection side may be abbreviated, making it possible to only adjust the mirror.

Furthermore, a mirror is not necessarily required, and following its assembly, not only the mirror unit, but the light source unit and the detector unit may also collaborate and be automatically driven.

In addition, with the present embodiment, among the light detectors position adjustment mechanisms were attached to the narrow angle scattered light detectors. However, position adjustment mechanisms may also be attached to wide-angle scattered light detectors.

Of course, with other components as well, it may be possible to change the shape or composition of the base structure, and the various light sources, within parameters which do not eliminate the essential components of the present invention, and it would be acceptable if each component of Embodiment 1 and 2 are appropriately assembled.

What is claimed is:

1. A particle size distribution analyzer comprising:
   a transparent cell which stores a particles dispersed in a dispersion medium;
   a light source which emits light to the particles within the transparent cell;
   multiple light detectors dispersed and arranged so as to detect the intensity of diffracted and/or scattered light from the light source;
   optical equipment arranged between the light source and the light detectors;
   a calculating part which calculates the particle size distribution of the particles on the optical intensity signal output from the light detector;
   a cell storage space which is configured to operatively mount and release the transparent cell; and
   an equipment storage space which stores the light source, the multiple light detectors, and the optical equipment, the equipment storage space has a sealed construction which is separated from the cell storage space,
   wherein, the optical equipment is provided with a projection lens which refracts the light from the light source and a mechanical openable shutter arranged between the light source and the projection lens, and a drive source for the shutter arranged outside of the equipment storage space.

2. The particle size distribution analyzer of claim 1 wherein power devices including motors and fans are arranged outside of the cell storage space and the sealed equipment storage space.

3. The particle size distribution analyzer of claim 1 further comprising a base construction body which accomplishes unitized construction and a couple of cases which are mutually separately arranged, using the base construction body, wherein the equipment storage space is formed by the cases in which the light source, the light detectors and the optical equipment are separately arranged, the cell storage space is arranged between the cases to operatively position the transparent cell.

4. The particle size distribution analyzer of claim 1 wherein in surfaces forming the cell storage space, at least two surfaces next to each other are provided with attached openable lids which can be respectively opened and closed, and configured in a state in which the lids, when opened, have two surfaces form a continuous aperture.

5. A particle size distribution analyzer comprising:
   a plurality of transparent cells which are configured to have particles dispersed in a dispersion medium;
   a light source which emits light onto the particles within the transparent cell;
   multiple light detectors dispersed and arranged so as to detect the intensity of diffracted and/or scattered light generated by the emission of light from the light source;
   a computer device which calculates the particle size distribution of the particles based on light intensity signals output from the light detectors; and
   a couple of cases being arranged to be mutually separated to provide apportioned storage of the light source in one case and light detectors in a second case, and a cell storage space which passes light to an opposing surface from one surface, being formed between the facing walls of both cases and configured to removably position any one of the plurality of transparent cells.

6. The particle size distribution analyzer of claim 5 further comprising a base construction body formed from an interim body and a standing support body which stands as a unit from both sides of the interim body, wherein the light source is supported by one standing support body and the light detectors is supported by the other standing support body, the cases are formed by at least one part of the standing support body.

7. The particle size distribution analyzer of claim 5 wherein, among surfaces forming the cell storage space, are attached openable lids capable of being open and shut on at least 2 surfaces which include either said one surface or its opposing surface, in addition to which the other surfaces are blocked so as to be able to seal the cell storage space.

8. The particle size distribution analyzer of claim 7 in which the 2 surfaces are the upper surface and front surface of the cell storage space.

9. The particle size distribution analyzer of claim 5 wherein there is an attached cell support mechanism which supports any one of the plurality of transparent cells movably in a pass-through direction, such that any one of the transparent cells can be selectively positioned in a light radiating position to which light is irradiated from the light source.

10. A method of manufacturing the particle size distribution analyzer having:
    a light source which irradiates light to the particles;
    a light detector which detects the intensity of diffracted or scattered light generated by the radiation of light;
    a calculating part which calculates the particle size distribution of the particles based on the output value from a light detector;
    a base construction body comprising a single product;
    a support body which forms a light source unit which supports as a unit the light source and projection lens arranged in front of the light source;
    a light track adjustment mechanism for adjusting the tracking of the light emitted from the light source attached to the light source unit; and
    position determination construction for positioning and attaching the light source unit and the light detectors in a specified position of the base construction body, comprising the steps of;
    adjusting the light track relative to the light source unit by the light track adjustment mechanism so as to be brought to within standards, by using a light tracking confirmation jig which is configured for recognizing when the light track from the light source unit is within standards; and
    attaching a post-adjustment light source unit to the base construction body.

11. A method of manufacturing the particle size distribution analyzer having:
    a light source which irradiates light to the particles;
    a light detector which detects the intensity of diffracted or scattered light generated by the radiation of light;
    a calculating part which calculates the particle size distribution of the particles based on the output value from the light detector;
    a base construction body comprising a single product;
    a support body which forms a light source unit which supports as a unit the light source and projection lens arranged in front of the light source;
    a light track adjustment mechanism for adjusting the tracking of the light emitted from the light source attached to the light source unit;
    a second support body which supports the light detectors, and forms the detector unit;
    a detector position adjustment mechanism for adjusting the light detectors unit to a predetermined position of the second support body; and
    position determination construction for positioning and attaching the light source unit and the light detector unit in a specified position of the base construction body, comprising the steps of;
    adjusting the relative position of the light detectors to the second support body by the detector position adjustment mechanism so as to be brought to within standards, by using a detector position confirmation jig which is configured for recognizing whether the relative position of the light detectors are within standards; and
    attaching the post-adjustment light detector unit to the base construction body.

12. A particle size distribution analyzer comprising:
    a transparent cell which stores particles dispersed in a dispersion medium;
    a light source which emits light to the particles within the transparent cell;
    multiple light detectors are dispersed and arranged so as to detect the intensity of diffracted or scattered light from the light source;
    optical equipment is arranged between the light source and the light detectors;
    a calculating part calculates the particle size distribution of the particles on the optical intensity signal output from the light detectors;
    a cell storage space stores the transparent cell; and
    an equipment storage space stores the light source, the light detectors, and the optical equipment, the equipment storage space has a sealed construction which is separated from the cell storage space, and in surfaces forming the cell storage space, at least two surfaces next to each other are provided with attached openable lids which can be respectively opened and closed, in a state in which the openable lids are open, the two surfaces form a continuous aperture.

13. A particle size distribution analyzer comprising:
a transparent cell which stores particles dispersed in a dispersion medium;
a light source which emits light to the particles within the transparent cell;
multiple light detectors are dispersed and arranged so as to detect the intensity of diffracted or scattered light from the light source;
optical equipment is arranged between the light source and the light detectors;
a calculating part calculates the particle size distribution of the particles on the optical intensity signal output from the light detectors;
a cell storage space stores the transparent cell; and
an equipment storage space stores the light source, the light detectors, and the optical equipment, the equipment storage space has a sealed construction which is separated from the cell storage space, and the optical equipment is provided with a projection lens which refracts the light which broadens from the light source, further comprising a mechanical openable shutter being arranged between the light source and the projection lens, and a drive source for the shutter is arranged on an outside of the equipment storage space.

14. A particle size distribution analyzer comprising:
a transparent cell which stores particles dispersed in a dispersion medium;
a light source which emits light onto the particles within the transparent cell;
multiple light detectors are dispersed and arranged so as to detect the intensity of diffracted or scattered light generated by the emission of light from the light source;
a computer device calculates the particle size distribution of the particles based on light intensity signals output from the light detectors;
a couple of cases being arranged to be mutually separated to provide apportioned storage of the light source and light detectors, and a cell storage space which passes to an opposing surface from one surface being formed between facing walls of both cases, and wherein, among surfaces forming the cell storage space, are attached openable lids capable of being open and shut on at least two surfaces which include either said one surface or its opposing surface, in addition to which the other surfaces are blocked and configured so as to be able to seal the cell storage space when the openable lid is closed.

15. A particle size distribution analyzer comprising:
a transparent cell which stores particles dispersed in a dispersion medium;
a light source which emits light onto the particles within the transparent cell;
multiple light detectors dispersed and arranged so as to detect the intensity of diffracted or scattered light generated by the emission of light from the light source, a computer device which calculates the particle size distribution of the particles based on light intensity signals output from the light detectors,
a couple of cases being arranged to be mutually separated, which provide apportioned storage of the light source and light detectors, and a cell storage space which passes to an opposing surface from one surface, being formed between the facing walls of both cases, and wherein, among surfaces forming the cell storage space, are attached openable lids capable of being open and shut on at least two surfaces which include either said one surface or its opposing surface, in addition to which the other surfaces are blocked, and configured to be able to seal the cell storage space, in which the two surfaces are the upper surface and front surface of the cell storage space.

16. A particle size distribution analyzer comprising:
a transparent cell which stores particles dispersed in a dispersion medium;
a light source which emits light onto the particles within the transparent cell;
multiple light detectors are dispersed and arranged so as to detect the intensity of diffracted or scattered light generated by the emission of light from the light source;
a computer device calculates the particle size distribution of the particles based on light intensity signals output from the light detectors; and
a couple of cases are arranged to be mutually separated and provide apportioned storage of the light source and light detectors, and a cell storage space which passes to an opposing surface from one surface, being formed between facing walls of both cases, wherein there is an attached cell support mechanism which supports multiple cells movably in a pass-through direction and configured such that any one of the cells can be selectively positioned in the light radiating position to which light is irradiated from the light source.

17. A particle size distribution analyzer system comprising:
a base unit;
a first light projecting source unit mounted on the base unit;
a second light detection unit mounted on the base unit to detect and provide light from the first light projecting source unit;
a movable sample cell;
a sample cell support mechanism is operatively mounted between the first light projecting source unit and the second light detecting unit to removably fasten and release the movable sample cell in an operative position to receive light from the first light projecting source unit and transmit light through the movable sample cell to the second light detecting unit, wherein the movable sample cell can be replaced with another member sample cell; and
a computer unit is configured to process the light signals provided by the second light detecting unit after contact with a sample in the movable sample cell to determine a particle size distribution.

18. The particle size distribution analyzer system of claim 17 wherein the sample cell support mechanism includes a mounting member for releasable attachment to the movable sample cell, the mounting member is configured to translate, between the first light projecting source unit and the second light detecting unit, the movable sample cell to the operative position.

19. The particle size distribution analyzer system of claim 17 further including an openable lid unit for removably covering a vertical opening between the first light projecting source unit and the second light detecting unit to enclose the sample cell support mechanism.

20. The particle size distribution analyzer system of claim 17 wherein the sample cell support mechanism is mounted on the base unit.

21. The particle size distribution analyzer system of claim 17 wherein the first light projecting source unit and the second light detecting unit are sealed from the sample cell support mechanism and the movable sample cell.

22. The particle size distribution analyzer system of claim 17 further including an electrical power unit movably mounted on the base unit to power the first light projecting source unit and the second light detecting unit.

23. The particle size distribution analyzer system of claim 17 wherein the base unit is a unitary construction of a U-shaped form having a laterally extending base and upward extending support bodies at opposite ends of the laterally extending base to form at least outer walls of the first light projecting source unit and the second light detecting detecting unit.

24. The particle size distribution analyzer system of claim 17 wherein a plurality of different types of movable sample cells can be mounted on the sample cell support mechanism including wet flow cells, wet batch cells, dry batch cells and dry flow cells.

25. A particle size distribution analyzer system comprising:
 a base unit;
 a sealed first means for projecting light and positioned on the base unit;
 a sealed second means for detecting light and positioned on the base unit;
 a plurality of sample cells;
 means for removably mounting and operatively positioning one of the plurality of sample cells in a position on the base unit configured to receive the projecting light and transmit the light through one of the plurality of sample cells for detection; and
 a computer unit configured to process the light detected to determine a particle size distribution in the one of the mounted plurality of sample cells.

26. The particle size distribution analyzer system of claim 25 further including an electrical power unit movably mounted on the base unit to power the first means and the second means.

27. The particle size distribution analyzer system of claim 25 wherein a plurality of different types of movable sample cells can be mounted on the sample cell support mechanism including wet flow cells, wet batch cells, dry batch cells and dry flow cells.

* * * * *